United States Patent
Waters et al.

(10) Patent No.: US 11,318,149 B2
(45) Date of Patent: May 3, 2022

(54) COMPOSITIONS AND METHODS FOR INHIBITING BIOFILM-FORMING BACTERIA

(71) Applicant: Board of Trustees of Michigan State University, East Lansing, MI (US)

(72) Inventors: Christopher Waters, East Lansing, MI (US); Michael Maiden, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 16/583,300

(22) Filed: Sep. 26, 2019

(65) Prior Publication Data

US 2020/0276214 A1    Sep. 3, 2020

Related U.S. Application Data

(60) Provisional application No. 62/737,407, filed on Sep. 27, 2018.

(51) Int. Cl.

| | | |
|---|---|---|
| *A61K 31/609* | (2006.01) | |
| *A61K 31/7036* | (2006.01) | |
| *A61K 31/65* | (2006.01) | |
| *A61P 31/04* | (2006.01) | |
| *A61K 9/00* | (2006.01) | |
| *A61P 11/00* | (2006.01) | |
| *A61K 38/17* | (2006.01) | |

(52) U.S. Cl.
CPC .......... *A61K 31/609* (2013.01); *A61K 9/0073* (2013.01); *A61K 31/65* (2013.01); *A61K 31/7036* (2013.01); *A61K 38/1767* (2013.01); *A61P 11/00* (2018.01); *A61P 31/04* (2018.01)

(58) Field of Classification Search
CPC .. A61K 31/609; A61K 31/65; A61K 31/7036; A61P 31/04
See application file for complete search history.

(56) References Cited

U.S. PATENT DOCUMENTS

| | | | |
|---|---|---|---|
| 2010/0092526 A1* | 4/2010 | Baker, Jr. | A61K 31/047 424/400 |
| 2016/0000748 A1* | 1/2016 | Page | A61K 47/10 514/460 |

FOREIGN PATENT DOCUMENTS

WO    WO-2019058268 A1 *   3/2019   ........... A61K 9/0017

OTHER PUBLICATIONS

Costabile et al (Molecular Pharmaceutics, 2015, vol. 12, pp. 2604-2617) (Year: 2015).*
Dosler et al (Journal of Chemotherapy, 2015, pp. 1-9) (Year: 2015).*
Picoli et al (Microbial Pathogenesis, 2017, vol. 112, pp. 57-62) (Year: 2017).*
Henry-Stanley et al (Journal of Medical Microbiology, 2014, vol. 63, pp. 861-869) (Year: 2014).*

* cited by examiner

*Primary Examiner* — Mark V Stevens
(74) *Attorney, Agent, or Firm* — Foley Hoag LLP

(57) ABSTRACT

The present disclosure provides, among other things, compositions and methods useful for inhibiting biofilm-forming bacteria. For example, the compositions and methods described herein can be used to inhibit the proliferation, viability, and/or biofilm-forming activity, of biofilm-forming bacteria.

14 Claims, 20 Drawing Sheets

COMPOSITIONS AND METHODS FOR INHIBITING BIOFILM-FORMING BACTERIA

RELATED APPLICATION

This application claims the benefit of priority to U.S. Provisional Patent Application No. 62/737,407, filed Sep. 27, 2018, which is hereby incorporated by reference in its entirety.

GOVERNMENT SUPPORT

This invention was made with government support under GM109259 and under GM110444 awarded by the National Institutes of Health. The government has certain rights in the invention.

BACKGROUND

Bacterial biofilm formation is a major cause of morbidity and mortality since such biofilm-based communities of bacteria can resist not only antibiotic treatment, but also clearance by the immune system. Biofilms are tolerant to antibiotic therapy and rapidly repopulate once antibiotic use is discontinued. The tolerance can be attributed to a number of factors, such as the physical structure of the biofilm and physiological state of biofilm-producing bacteria. For at least these reasons, new treatment strategies are needed to prevent and resolve infections by biofilm-forming bacteria.

SUMMARY

The present disclosure is based, at least in part, on the discovery of combinations of compounds that exhibit a synergistic effect in inhibiting biofilm-forming bacteria. Specifically, salicylanilide anthelmintic, oxyclozanide, combined with tobramycin, significantly increased killing of 24-hr *P. aeruginosa* biofilms. This combination also significantly accelerated the killing of cells within 24-hr biofilms and was effective against 4/6 CF clinical isolates tested, including a tobramycin resistant strain. Additionally, oxyclozanide combined with other aminoglycosides and tetracycline were significantly more effective against 24-hr biofilms. The compositions and methods described herein are also useful in preventative applications, such as pretreatment of surgical tools, bandages, surfaces, and the like to inhibit biofilm-forming bacterial growth.

Accordingly, in one aspect, the disclosure features a method for inhibiting biofilm-forming bacteria. The method comprises contacting the bacteria with an effective amount of: (i) a first agent (e.g., an aminoglycoside or a tetracycline) and (ii) a salicylanilide or a derivative thereof, to thereby inhibit the bacteria. Inhibition of the bacteria can be, e.g., inhibition of the proliferation, viability, or biofilm-forming activity of the biofilm-forming bacteria.

In another aspect, the disclosure features a method for treating a subject who is infected with biofilm-forming bacteria, which method comprises administering to the subject an effective amount of: a first agent (e.g., an aminoglycoside or a tetracycline) and (ii) a salicylanilide or a derivative thereof, thereof, to thereby inhibit the proliferation, viability, or biofilm-forming activity of the biofilm-forming bacteria.

In another aspect, the disclosure features a method for ameliorating the signs and/or symptoms of an infection with biofilm-forming bacteria in a subject. The method comprises administering to the subject an effective amount of: (i) a first agent (e.g., an aminoglycoside or a tetracycline) and (ii) a salicylanilide or a derivative thereof to thereby inhibit the proliferation, viability, or biofilm-forming activity of the biofilm-forming bacteria.

In another aspect, the disclosure features an a first agent (e.g., an aminoglycoside or a tetracycline) for use in inhibiting biofilm-forming bacteria (or for treating a subject who is infected with biofilm-forming bacteria; or for ameliorating the signs and/or symptoms of an infection with biofilm-forming bacteria in a subject), wherein the aminoglycoside is to be used in conjunction with and (ii) a salicylanilide or a derivative thereof.

In some embodiments of any of the methods or compositions described herein, the subject is a human. In some embodiments of any of the methods or compositions described herein, the subject is a non-human mammal, such as a non-human primate (e.g., macaque, orangutan, chimpanzee, gorilla, or lemur), a type of domesticated livestock (e.g., pig, sheep, goat, or cow), cat, dog, or rodent. In some embodiments, the subject is a bird (e.g., chicken, turkey, quail, or pheasant).

In some embodiments of any of the methods or compositions described herein, the subject has a respiratory condition, such as cystic fibrosis (CF), chronic obstructive pulmonary disease, bronchitis, asthma, bronchial asthma, pulmonary fibrosis, emphysema, an interstitial pulmonary disorder, or pneumonia. In some embodiments of any of the methods or compositions described herein, the subject has CF and pneumonia.

In some embodiments of any of the methods or compositions described herein, the subject has a wound, such as a chronic wound or a chronic non-healing wound. In some embodiments of any of the methods or compositions described herein, the subject has an ocular infection, e.g., otitis media or conjunctivitis. In some embodiments of any of the methods or compositions described herein, the subject has a urinary tract infection. In some embodiments of any of the methods or compositions described herein, the subject has endocarditis.

In some embodiments of any of the methods or compositions described herein, the subject has an implant (e.g., an oral implant, a pacemaker or an internal prosthetic (e.g., an artificial hip or knee)) that is infected with biofilm-forming bacteria.

In some embodiments, one or both of the first agent (e.g., an aminoglycoside or a tetracycline) and salicylanilide or a derivative thereof are applied to a surface, e.g., surgical tools or surfaces, kitchen or bathroom surfaces, implants, or medical clothing or bandages. In some embodiments, one or both of the first agent (e.g., an aminoglycoside or a tetracycline) and salicylanilide or a derivative thereof are perfused into an organ for transplantation. In some embodiments, an organ can be soaked, stored, or transported in a solution comprising one or both of the first agent (e.g., an aminoglycoside or a tetracycline) and salicylanilide or a derivative thereof, prior to transplantation. In some embodiments, one or both of the first agent (e.g., an aminoglycoside or a tetracycline) and salicylanilide or a derivative thereof can be present in toothpaste or gel, mouthwash, eye drops, anti-bacterial wipes, soap, shampoo, contact lens solution, ear drops, cosmetics, skin lotion, or an anti-microbial spray or aerosol.

In some embodiments of any of the methods or compositions described herein, the biofilm-forming bacteria are gram negative. In some embodiments of any of the methods or compositions described herein, the biofilm-forming bacteria are gram positive.

In some embodiments of any of the methods or compositions described herein, the biofilm-forming bacteria are of the genus *Pseudomonas*, e.g., *Pseudomonas aeruginosa*.

In some embodiments of any of the methods or compositions described herein, the biofilm-forming bacteria are *Actinobacillus actinomycetemcomitans, Acinetobacter baumannii, Bordetella pertussis, Brucella* sp., *Campylobacter* sp., *Capnocytophaga* sp., *Cardiobacterium hominis, Eikenella corrodens, Francisella tularensis, Haemophilus ducreyi, Haemophilus influenzae, Helicobacter pylori, Kingella kingae, Legionella pneumophila, Pasteurella multocida, Citrobacter* sp., *Enterobacter* sp., *Escherichia coli, Klebsiella pneumoniae, Proteus* sp., *Salmonella enteriditis, Salmonella typhi, Serratia marcescens, Shigella* sp., *Yersinia enterocolitica, Yersinia pestis, Neisseria gonorrhoeae, Neisseria meningitidis, Moraxella catarrhalis, Veillonella* sp., *Bacteroides fragilis, Bacteroides* sp., *Prevotella* sp., *Fusobacterium* sp., *Spirillum minus, Aeromonas* sp., *Plesiomonas shigelloides, Vibrio cholerae, Vibrio parahaemolyticus, Vibrio vulnificus, Mycobacterium tuberculosis, Acinetobacter* sp., *Flavobacterium* sp., *Pseudomonas aeruginosa, Burkholderia cepacia, Burkholderia pseudomallei, Xanthomonas maltophilia, Stenotrophomonas maltophila, Staphylococcus aureus, Bacillus* spp., *Clostridium* spp., or *Streptococcus* spp.

In some embodiments, the biofilm forming bacteria are multi-drug resistant pathogens (e.g., a multi-drug resistant strain of *Enterococcus faecium, Staphylococcus aureus, Klebsiella pneumoniae, Acinetobacter baumanii, Pseudomonas aeruginosa*, or *Enterobacter* species).

In some embodiments, the salicylanilide is oxyclozanide. In some embodiments, the salicylanilide is niclosamide, rafoxanide, or bromochlorosalicylanilide. In some embodiments, the salicylanilide or a derivative thereof is contacted to the bacteria or administered as a composition comprising at least of an amount of salicylanilide or a derivative thereof (e.g., at least 50 µM, at least 100 µM, at least 200 µM, at least 300 µM, or at least 400 µM salicylanilide or a derivative thereof).

In some embodiments, the first agent is an aminoglycoside. In some embodiments of any of the methods or compositions described herein, the aminoglycoside is tobramycin. In some embodiments of any of the methods or compositions described herein, the aminoglycoside is gentamicin. In some embodiments of any of the methods or compositions described herein, the aminoglycoside is kanamycin, streptomycin, netilmicin, neomycin A, neomycin B, neomycin C, neomycin E, amikacin, bibekacin, sisomycin, or new antibiotics thereof.

In some embodiments of any of the methods or compositions described herein, the effective amount of the aminoglycoside is less than the amount of the aminoglycoside required for the same level of effectiveness in the absence of a salicylanilide or a derivative thereof. In some embodiments of any of the methods or compositions described herein, the effective amount of the aminoglycoside is less than or equal to 50% of the amount of the aminoglycoside required for the same level of effectiveness in the absence of a salicylanilide or a derivative thereof. In some embodiments of any of the methods or compositions described herein, the effective amount of the aminoglycoside is less than or equal to 25% of the amount of the aminoglycoside required for the same level of effectiveness in the absence of a salicylanilide or a derivative thereof.

In some embodiments of any of the methods or compositions described herein, the aminoglycoside is contacted to the bacteria or administered as a composition comprising at least 50 µM of the aminoglycoside. In some embodiments of any of the methods or compositions described herein, the aminoglycoside is contacted to the bacteria or administered as a composition comprising at least 100 µM of the aminoglycoside. In some embodiments of any of the methods or compositions described herein, the aminoglycoside is contacted to the bacteria or administered as a composition comprising at least 200 µM of the aminoglycoside. In some embodiments of any of the methods or compositions described herein, the aminoglycoside is contacted to the bacteria or administered as a composition comprising at least 400 µM of the aminoglycoside.

In some embodiments of any of the methods or compositions described herein, tobramycin is contacted to the bacteria or is administered as a composition comprising at least 50 µM of tobramycin. In some embodiments of any of the methods or compositions described herein, tobramycin is contacted to the bacteria or is administered as a composition comprising at least 100 µM of tobramycin. In some embodiments of any of the methods or compositions described herein, tobramycin is contacted to the bacteria or is administered as a composition comprising at least 200 µM of tobramycin. In some embodiments of any of the methods or compositions described herein, tobramycin is contacted to the bacteria or is administered as a composition comprising at least 400 µM of tobramycin.

In some embodiments of any of the methods or compositions described herein, the first agent (e.g., an aminoglycoside or a tetracycline) and the salicylanilide or a derivative thereof, are administered conjointly.

In some embodiments, the first agent is a tetracycline. In some embodiments of any of the methods or compositions described herein, tetracycline is contacted to the bacteria or is administered as a composition comprising at least 50 µM of tetracycline. In some embodiments of any of the methods or compositions described herein, tetracycline is contacted to the bacteria or is administered as a composition comprising at least 100 µM of tetracycline. In some embodiments of any of the methods or compositions described herein, tetracycline is contacted to the bacteria or is administered as a composition comprising at least 200 µM of tetracycline. In some embodiments of any of the methods or compositions described herein, tetracycline is contacted to the bacteria or is administered as a composition comprising at least 400 µM of tetracycline.

In some embodiments of any of the methods or compositions described herein, the first agent (e.g., an aminoglycoside or a tetracycline) is administered as an aerosol.

In some embodiments of any of the methods or compositions described herein, the first agent (e.g., an aminoglycoside or a tetracycline) is orally administered to the subject.

In some embodiments of any of the methods or compositions described herein, the first agent (e.g., an aminoglycoside or a tetracycline) is parenterally administered to the subject.

In some embodiments of any of the methods or compositions described herein, the salicylanilide or a derivative thereof is administered as an aerosol.

In some embodiments of any of the methods or compositions described herein, the salicylanilide or a derivative thereof is orally administered to the subject.

In some embodiments of any of the methods or compositions described herein, the salicylanilide or a derivative thereof is administered topically.

In some embodiments of any of the methods or compositions described herein, the salicylanilide or a derivative thereof is parenterally administered to the subject.

Salicylanilide or a derivative thereof may be administered in any dose, for example, the salicylanilide or a derivative thereof may be administered at a rate of at least 1 mg/kg (e.g., at least 2 mg/kg, at least 3 mg/kg, at least 5 mg/kg, at least 10 mg/kg, at least 25 mg/kg, at least 50 mg/kg, at least 100 mg/kg, at least 150 mg/kg, at least 200 mg/kg, at least 250 mg/kg, at least 400 mg/kg, at least 500 mg/kg, or at least 750 mg/kg, or at least 1000 mg/kg.

In another aspect, the disclosure features a method for treating a subject who is infected with *Pseudomonas aeruginosa*. The method comprises administering to the subject an effective amount of a first agent and a salicylanilide or derivative thereof, to thereby treat the *Pseudomonas aeruginosa* infection. In some embodiments, the first agent is an aminoglycoside. In some embodiments, the aminoglycoside is tobramycin or gentamicin. In some embodiments, the first agent is a tetracycline.

In yet another aspect, the disclosure features a first agent (e.g., an aminoglycoside or a tetracycline) for use in treating a subject who is infected with *Pseudomonas aeruginosa*, wherein the first agent is to be used in conjunction with the salicylanilide or derivative thereof.

In another aspect, the disclosure features a first agent (e.g., an aminoglycoside or a tetracycline) for use in treating a subject who is infected with *Pseudomonas aeruginosa*, wherein the first agent is to be used in conjunction with the salicylanilide or derivative thereof.

In some embodiments of any of the methods or compositions described herein, the subject is a human.

In some embodiments of any of the methods or compositions described herein, the subject has CF or CF with pneumonia.

In some embodiments of any of the methods or compositions described herein, the effective amount of the aminoglycoside is no greater than 10,000 mg per day. In some embodiments of any of the methods or compositions described herein, the effective amount of the aminoglycoside is no greater than 5000 mg per day. In some embodiments of any of the methods or compositions described herein, the effective amount of the aminoglycoside is no greater than 2000 mg per day. In some embodiments of any of the methods or compositions described herein, the effective amount of the aminoglycoside is no greater than 1000 mg per day. In some embodiments of any of the methods or compositions described herein, the effective amount of the aminoglycoside is no greater than 600 mg per day. In some embodiments of any of the methods or compositions described herein, the effective amount of the aminoglycoside is no greater than 300 mg per day. In some embodiments of any of the methods or compositions described herein, the effective amount of the aminoglycoside is no greater than 150 mg per day. In some embodiments of any of the methods or compositions described herein, the effective amount of the aminoglycoside is no greater than 125 mg per day. In some embodiments of any of the methods or compositions described herein, the effective amount of the aminoglycoside is no greater than 100 mg per day. In some embodiments of any of the methods or compositions described herein, the effective amount of the aminoglycoside is no greater than 75 mg per day. In some embodiments of any of the methods or compositions described herein, the effective amount of the aminoglycoside is no greater than 50 mg per day. In some embodiments of any of the methods or compositions described herein, the effective amount of the aminoglycoside is no greater than 25 mg per day.

Also provided herein are methods for inhibiting the proliferation, viability, or biofilm-forming activity of biofilm-forming bacteria by contacting the bacteria with an effective amount of: (i) an aminoglycoside and (ii) melittin, to thereby inhibit the proliferation, viability, or biofilm-forming activity of the biofilm-forming bacteria.

In another aspect, provided herein are methods for treating a subject who is infected with biofilm-forming bacteria by administering to the subject an effective amount of: (i) a an aminoglycoside and (ii) melittin, to thereby inhibit the proliferation, viability, or biofilm-forming activity of the biofilm-forming bacteria.

In yet another aspect provided herein are methods for ameliorating the signs or symptoms of an infection with biofilm-forming bacteria in a subject by administering to the subject an effective amount of: (i) an aminoglycoside and (ii) melittin, to thereby inhibit the proliferation, viability, or biofilm-forming activity of the biofilm-forming bacteria.

The aminoglycoside may be tobramycin or gentamicin, or any other aminoglycoside disclosed herein. The bacteria may be *P. aeruginosa* or *Staph aureus*, or any other bacteria disclosed herein.

The agents and compounds provided herein may be administered according to any route of administration known in the art. The agents and compounds of the invention may be administered in the same compound or in different compounds.

Melittin may be administered in any dose, for example, the melittin may be administered at a rate of at least 1 mg/kg (e.g., at least 2 mg/kg, at least 3 mg/kg, at least 5 mg/kg, at least 10 mg/kg, at least 25 mg/kg, at least 50 mg/kg, at least 100 mg/kg, at least 150 mg/kg, at least 200 mg/kg, at least 250 mg/kg, at least 400 mg/kg, at least 500 mg/kg, or at least 750 mg/kg, or at least 1000 mg/kg.

Unless otherwise defined, all technical and scientific terms used herein have the same meaning as commonly understood by one of ordinary skill in the art to which this disclosure pertains. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Other features and advantages of the present disclosure, e.g., methods for inhibiting bacterial growth, will be apparent from the following description, the examples, and from the claims.

DETAILED DESCRIPTION

Figure 1:
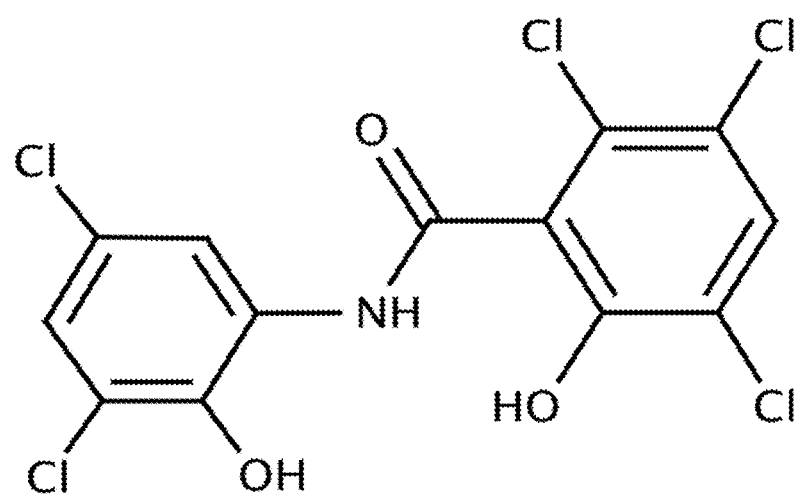
FIG. 1 depicts the chemical structure of salicylanillide anthelmintic oxyclozanide.

The present disclosure provides, among other things, compositions and methods useful for inhibiting biofilm-forming bacteria. For example, the compositions and methods described herein can be used to inhibit the proliferation or viability of biofilm-forming bacteria. The compositions (which can be used in in vitro, ex vivo, and in vivo applications) can also be used to inhibit the biofilm-forming activity of biofilm-forming bacteria. While in no way limiting, exemplary compositions and methods are elaborated on below.

Definitions

For convenience, certain terms employed in the specification, examples, and appended claims are collected here.

The articles "a" and "an" are used herein to refer to one or to more than one (i.e., to at least one) of the grammatical object of the article.

As used herein, the term "administering" means providing an agent or composition to a subject, and includes, but is not limited to, administering by a medical professional and self-administering.

As used herein, the term "subject" means a human or non-human animal selected for treatment or therapy. In certain embodiments, of the methods and compositions described herein the subject is a human subject.

"Treating" a disease in a subject or "treating" a subject having a disease refers to subjecting the subject to a pharmaceutical treatment, e.g., the administration of a drug, such that at least one symptom of the disease is decreased or prevented from worsening.

Compositions

As used herein, the term "aminoglycoside" refers to any naturally occurring drug, or semi-synthetic or synthetic derivative, comprising a highly-conserved aminocyclitol ring, which is a central scaffold that is linked to various amino-modified sugar moieties, and that inhibits biofilm-forming bacteria. The aminocyclitol ring is comprised primarily of 2-deoxystreptamine (2-DOS) and has 1,3-diamino functionality and three or four hydroxyl groups that provide anchoring points for aminosugar moities. Aminoglycosides can be divided into three subclasses depending on the substitution pattern: 4-monosubstituted, or 4,5- or 4,6-disubstituted. Aminoglycosides in each subclass show close structural resemblance. Aminoglycosides have several mechanisms of antibiotic activity, including, but not limited to, inhibition of protein synthesis; interfering with proofreading processes during translation, and causing increased rate of error in synthesis with premature termination; inhibition of ribosomal translocation where the peptidyl-tRNA moves from the A-site to the P-site; disruption of bacterial cell membrane integrity; and/or binding to bacterial 30S ribosomal subunit.

In some embodiments, the aminoglycoside can be, e.g., erythromycin, clarithromycin, streptomycin, gentamicin, kanamycin A, tobramycin, neomycin B, neomycin C, framycetin, paromomycin, ribostamycin, amikacin, arbekacin, azithromycin, bekanamycin (kanamycin B), dibekacin, spectinomycin, hygromycin B, paromomycin sulfate, dihydrostreptomycin, netilmicin, sisomicin, isepamicin, verdamicin, astromicin, neamine, ribostamycin, vancomycin, paromomycin, or lividomycin. In some embodiments, the aminoglycoside is tobramycin. In some embodiments, the aminoglycoside is gentamicin.

Salicylanilide is a chemical compound which is the amide of salicylic acid and aniline. It is classified as both a salicylamide and an anilide. Derivatives of salicylanilide have a variety of pharmacological uses. Chlorinated derivatives including niclosamide, oxyclozanide, and rafoxanide are used as anthelmintics, especially as flukicides. Brominated derivatives including dibromsalan, metabromsalan, and tribromsalan are used as disinfectants with antibacterial and antifungal activities. The structure of oxyclozanide is set forth in FIG. 1. The skeletal formula for salicylamide is below.

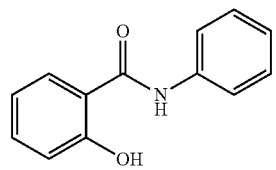 [SMILES: O=C(Nc1ccccc1)c1ccccc1O]

Examples of salicylanilide derivatives are described in, e.g., U.S. Pat. Nos. 4,025,647, 4,005,218, the disclosures of each of which are incorporated herein by reference in their entirety.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier.

Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation of pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation), compound or agent disclosed herein can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973; 5,763,493; 5,731,000; 5,541,231; 5,427,798; 5,358,970; and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a par- enterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

A nebulizer of the present application can be a jet air nebulizer (e.g., Pari LC Jet Plus or Hudson T Up-draft II), an ultrasonicnebulizer (e.g., MABISMist II), a vibrating mesh nebulizer (e.g., Micro air by Omron) and a Shockwave nebulizer (EvitLabs Sonik LDI20). As used herein, an "aerosol composition" or like grammatical terms means an inhibitor described herein in a form or formulation that is suitable for pulmonary delivery. The aerosol composition may be in the dry powder form, it may be a solution, suspension or slurry to be nebulized, or it may be in admixture with a suitable low boiling point, highly volatile propellant. It is to be understood that more than one inhibitor and optionally other active agents or ingredients may be incorporated into the aerosolized formulation or aerosol composition.

In certain preferred embodiments, an active agent (e.g., an inhibitor described herein) retains more than 50% of its activity after nebulization, preferably more than 70%. In certain preferred embodiments, an active agent (e.g., an inhibitor described herein) more than 50% of its purity after nebulization, preferably more than 70%.

Active agent formulations suitable for use in the present application include dry powders, solutions, suspensions or slurries for nebulization and particles suspended or dissolved within a propellant. Dry powders suitable for use in the present application include amorphous active agents, crystalline active agents and mixtures of both amorphous and crystalline active agents. The dry powder active agents have a particle size selected to permit penetration into the alveoli of the lungs, that is, preferably 10 µm mass median diameter $(MMD)_5$ preferably less than 7.5 µm, and most preferably less than 5 µm, and usually being in the range of 0.1 µm to 5 µm in diameter. The delivered dose efficiency (DDE) of these powders is >30%, usually >40%, preferably >50 and often >60% and the aerosol particle size distribution is about 1.0-5.0 µm mass median aerodynamic diameter (MMAD), usually 1.5-4.5 µm MMAD and preferably 1.5-4.0 µm MMAD. These dry powder active agents have a moisture content below about 10% by weight, usually below about 5% by weight, and preferably below about 3% by weight. Such active agent powders are described in WO 95/24183 and WO 96/32149, which are incorporated by reference herein.

Dry powder active agent formulations are preferably prepared by spray drying under conditions which result in a substantially amorphous powder. Bulk active agent, usually in crystalline form, is dissolved in a physiologically acceptable aqueous buffer, typically a citrate buffer having a pH range from about 2 to 9. The active agent is dissolved at a concentration from 0.01% by weight to 1% by weight, usually from 0.1% to 0.2%. The solutions may then be spray dried in a conventional spray drier available from commercial suppliers such as Niro A/S (Denmark), Buchi (Switzerland) and the like, resulting in a substantially amorphous powder. These amorphous powders may also be prepared by lyophilization, vacuum drying, or evaporative drying of a suitable active agent solution under conditions to produce the amorphous structure. The amorphous active agent formulation so produced can be ground or milled to produce particles within the desired size range.

Dry powder active agents may also be in a crystalline form. The crystalline dry powders may be prepared by grinding or jet milling the bulk crystalline active agent. The active agent powders of the present application may optionally be combined with pharmaceutical carriers or excipients which are suitable for respiratory and pulmonary administration. Such carriers may serve simply as bulking agents when it is desired to reduce the active agent concentration in the powder which is being delivered to a patient, but may also serve to improve the dispersability of the powder within a powder dispersion device in order to provide more efficient and reproducible delivery of the active agent and to improve handling characteristics of the active agent such as flowability and consistency to facilitate manufacturing and powder filling. Such excipients include but are not limited to (a) carbohydrates, e.g., monosaccharides such as fructose, galactose, glucose, D-mannose, sorbose, and the like; disaccharides, such as lactose, trehalose, cellobiose, and the like; cyclodextrins, such as 2-hydroxypropyl-.beta.-cyclodextrin; and polysaccharides, such as raffmose, maltodextrins, dextrans, and the like; (b) amino acids, such as glycine, arginine, aspartic acid, glutamic acid, cysteine, lysine, and the like; (c) organic salts prepared from organic acids and bases, such as sodium citrate, sodium ascorbate, magnesium gluconate, sodium gluconate, tromethamin hydrochloride, and the like; (d) peptides and proteins such as aspartame, human serum albumin, gelatin, and the like; and (e) alditols, such as mannitol, xylitol, and the like. A preferred group of carriers includes lactose, trehalose, raffmose, maltodextrins, glycine, sodium citrate, human serum albumin and mannitol.

The dry powder active agent formulations may be delivered using Inhale Therapeutic Systems' dry powder inhaler as described in WO 96/09085 which is incorporated herein by reference, but adapted to control the flow rate at a desirable level or within a suitable range. The dry powders may also be delivered using a metered dose inhaler as described by Laube et al. in U.S. Pat. No. 5,320,094, which is incorporated by reference herein. Nebulized solutions may be prepared by aerosolizing commercially available active agent formulation solutions. These solutions may be delivered by a jet nebulizer such as the Raindrop, produced by Puritan Bennett, the use of which is described by Laube et al., supra. Other methods for delivery of solutions, suspensions of slurries are described by Rubsamen et al, U.S. Pat. No. 5,672,581. A device that uses a vibrating, piezoelectric member is described in Ivri et al., U.S. Pat. No. 5,586,550, which is incorporated by reference herein.

Propellant systems may include an active agent dissolved in a propellant or particles suspended in a propellant. Both of these types of formulations are described in Rubsamen et al., U.S. Pat. No. 5,672,581, which is incorporated herein by reference. In certain embodiments, an aerosol or nebulization composition can be combined with one or more other aerosol or nebulization treatments, such as sympathomimetics (e.g., albuterol), antibiotics (e.g., tobramycin), deoxyribonucleases (e.g., pulmozyme), anticholinergic drugs (e.g., ipratropium bromide), or corticosteroids.

As described herein, an active agent (e.g., an inhibitor described herein) may be formulated as microparticles. Microparticles having a diameter of between 0.5 and 10 microns can penetrate the lungs, passing through most of the natural barriers. A diameter of less than ten microns is generally required to bypass the throat; a diameter of 0.5 microns or greater is usually required to avoid being exhaled.

In certain embodiments, an active agent (e.g., an inhibitor described herein) is formulated in a supramolecular complex, which may have a diameter of between 0.5 and 10 microns, which can be aggregated into particles having a diameter of between 0.5 and 10 microns.

In other embodiments, an active agent (e.g., an inhibitor described herein) are provided in liposomes or supramolecular complexes appropriately formulated for pulmonary delivery.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician, dentist, or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. The active compound will be administered at least once daily. The compounds, agents, and compositions disclosed herein may be administered every other say, weekly, or monthly.

The patient receiving this treatment is any animal in need, including primates, in particular humans, and other mammals such as equines, cattle, swine and sheep; and poultry and pets in general. In some embodiments, the compositions and kits described herein are to be used in veterinary applications, such as treating or preventing infections in or on domesticated livestock.

In certain embodiments, any compounds disclosed herein may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

In some embodiments, the compositions are formulated as an eye drop. In some embodiments, the compositions are formulated as an ointment, lotion, gel, cream, aerosol, spray, or salve. In some embodiments, the compositions comprise one or more antibiotics for use in treating bacterial infections.

The formulations may be presented as, for instance, ointments, creams or lotions, gels, eye ointments and eye or ear drops, sprays, impregnated dressings (e.g., bandages or dressings for use in would healing), and aerosols, and may contain appropriate conventional additives such as preservatives, solvents to assist drug penetration and emollients in ointments and creams. The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation. In some embodiments, the compounds are formulated for use in the eye. In some embodiments, the compounds are formulated for use in the ear. In some embodiments, the compounds are formulated for use on the skin, e.g., for treating chronic wounds, such as those associated with diabetes or other cardiovascular/circulatory disorders.

Exemplification

A major clinical obstacle in treating chronic infections is bacterial biofilm formation. On example of this is cystic fibrosis (CF), in which antibiotic treatment failure due to biofilms results in life-long infections by the Gram-negative opportunistic pathogen *Pseudomonas aeruginosa*. Current antibiotic therapies, such as tobramycin twice a day for 28-days, often fail to completely eradicate *P. aeruginosa*, allowing for pathoadpation to a chronic infectious state. Retrospective studies have shown that preventing this pathoadaptation, by improving initial interventions against transient *P. aeruginosa* infections can extend the lives of CF patients. We previously performed a high throughput screen to identify compounds that enhance tobramycin killing of cells within 24-hr biofilms formed by *P. aeruginosa*, and identified that the Food and Drug Administration approved salicylanilide anthelmintic, oxyclozanide, combined with tobramycin, significantly increased killing of 24-hr *P. aeruginosa* biofilms. This combination also significantly accelerated the killing of cells within 24-hr biofilms and was effective against 4/6 CF clinical isolates tested, including a tobramycin resistant strain. Additionally, oxyclozanide combined with other aminoglycosides and tetracycline were significantly more effective against 24-hr biofilms. Combination of these two FDA approved therapies could enhance the initial eradication of *P. aeruginosa* in CF patients and prevent the development of a chronic infectious state.

Cystic fibrosis (CF) is the most common life-shortening genetic disease in Caucasians. It affects 70,000 people worldwide and 30,000 people in the United States. CF is caused by a mutation in the cystic fibrosis transmembrane conductance regulator gene, resulting in a loss of a chloride channel and bicarbonate transport throughout the body. In the lungs, the loss of coordinated chloride and bicarbonate transport causes the airway mucus to become thick and dry, hindering the clearance of bacteria and debris. This immunological defect makes CF patients prone to recurrent lung infections, including several members of the multidrug-resistant (MDR) "ESKAPE" pathogens (*Enterococcus faecium, Staphylococcus aureus, Klebsiella pneumoniae, Acinetobacter baumanii, Pseudomonas aeruginosa*, and *Enterobacter* species).

By the mid-to-late teens, the dominant pathogen that colonizes the lungs of CF patients is *P. aeruginosa*. Central to this pathogen's success is its biofilm lifestyle, which results in a thick matrix surrounding the cells, leading to greatly enhanced resistance to antibacterial therapies, macrophages, and neutrophils. Treatment is further hindered by numerous antimicrobial resistance mechanisms found in *P. aeruginosa*, including efflux pumps, β-lactamases, and changes to outer membrane permeability. Additionally, *P. aeruginosa* evolves in the lungs of CF patients to form a "mucoid-type" biofilm that produces a thicker matrix, reducing the effectiveness of antibiotics by slowing their diffusion.

300 mg of nebulized tobramycin inhaled twice a day for 28 days in on-off cycles, reaching mean sputum concentrations of ~737 μg/g (~1,440 μM per dose), is currently the first line therapy for the eradication of *Pseudomonas* in CF patients. Despite the repeated use of high concentrations of tobramycin, it is estimated that more than half of all CF patients are chronically colonized with *P. aeruginosa* by adulthood. Retrospective studies have shown that the prevention and eradication of transient infections by *P. aeruginosa* before a chronic infectious state is underway can extend the lives of CF patients. Thus, new therapies that more effectively target this pathogen, especially as it transitions from an acute to chronic infection, would have a significant beneficial clinical outcome for CF patients.

To this end, we previously performed a high throughput screen (HTS) of 6,080 compounds from four drug repurposing libraries (Prestwick, MS2400, LOPAC, and focus collection libraries) at the University of Michigan Center for Chemical Genomics to identify novel compounds that enhanced tobramycin killing of mature *P. aeruginosa* biofilms. We determined that oxyclozanide, a Food and Drug Administration (FDA) approved drug for the treatment of parasitic worm infections in cattle, significantly enhance tobramycin killing of *P. aeruginosa* biofilms. We show that oxyclozanide and tobramycin accelerates killing of biofilms, is effective against a majority of CF clinical isolates, and generally enhances aminoglycoside effectiveness against biofilms. Our findings suggests that tobramycin combined with oxyclozanide could represent a potential new antimicrobial therapy for the treatment of *P. aeruginosa* biofilms in CF patients, as well as other biofilm-based *P. aeruginosa* infections such as diabetic foot ulcers and burn wounds.

Materials and Methods

Bacterial Strains, Culture Conditions, and Compounds

All strains used in this study are summarized in Table 1. The screen and experiments performed in this work, unless otherwise indicated, used PAO1, a strain of *P. aeruginosa* originally isolated from a wound in 1954. Clinical isolates were obtained from the Michigan State University (MSU) CF clinic. AMT0023_30 and AMT0023_34, were obtained from the *Pseudomonas* clinical reference panel, which were collected at the University of Washington CF clinic. Bacterial strains were grown in 8 mL glass test tubes (18×150 mm) at 35° C. in cation adjusted Müeller-Hinton Broth II (MHB, Sigma-Aldrich) with agitation at 210 revolutions per minute (RPM). Antibiotics and oxyclozanide were obtained from Sigma-Aldrich. Tobramycin sulfate, gentamicin sulfate, and streptomycin sulfate were dissolved in autoclaved deionized water and filter sterilized using 0.22 μM filter membranes (Thomas Scientific). Oxyclozanide and tetracycline were dissolved in 95% and 75% ethanol, respectively.

Minimum Inhibitory Concentration (MIC)

To measure antimicrobial susceptibility of planktonic cells, MICs were determined using the broth microdilution technique, as described previously. Briefly, microdilutions were made in a 96-well plate in 1% MHB diluted in Dulbecco's Phosphate Buffered Saline with magnesium and calcium (DPBS, Sigma-Aldrich). Cells were combined with the serial dilutions in the 96-well plate at a concentration of ~1×10⁶ CFU/mL in 10% MHB. The plates were then incubated for 24-hrs at 35° C. in a humidified chamber with agitation at 150 RPM. MIC breakpoints were chosen as the minimum concentration in which no turbidity greater than background was measured (absorbance at 595 nm), using a SpectraMax M5 microplate spectrophotometer system (Molecular Devices Sunnyvale, Calif.

Biofilm Susceptibility Testing Using BacTiter-Glo™

To measure antimicrobial susceptibility of biofilms, the MBEC™ assay was used (Innovotech) as previously described. This assay consists of a lid with 96 polystyrene pegs used to grow biofilms. Briefly, an overnight culture was washed and diluted to an $OD_{600}$ of 0.001 and seeded into a MBEC™ plate. To grow biofilms, the plate was then incubated for 24-hrs at 35° C. in a humidified chamber with agitation at 150 RPM. After 24-hrs, the lid was then transferred to a 96-well plate filled with DPBS and washed for 5-mins to remove non-adherent cells. The lid was transferred to the 96-well treatment plate and incubated for the indicated time points at 35° C. without agitation. After the incubation, the MBEC™ lid was washed and transferred to a black 96-well ViewPlate (PerkinElmer) filled with BacTiter-Glo™ to enumerate cell viability and then luminescence was measured using a EnVison Multilabel Plate Reader (PerkenElmer, Waltham, Mass.). Percent killing was calculated as:

$$\% \text{ Killing of Biofilm} = 1 - \left(\frac{\text{Luminesces of Treated Biofilm} - \text{Background}}{\text{Luminesces of Untreated Biofilm} - \text{Background}}\right) \times 100.$$

Dose response curves were performed in the same manner.

Crystal Violet Staining

To study biofilm dispersal under static conditions, crystal violet staining was performed as previously described. Briefly, 24-hr old biofilms formed on MBEC™ plates, as described above, were stained with crystal violet after a 6-hr incubation with oxyclozanide and tobramycin.

Time Killing Curves

Time killing curves were performed by growing 24-hr old biofilms on MBEC™ plates as previously described. Briefly, 100 µM of oxyclozanide and 500 µM of tobramycin were used to test for synergy at high concentrations of tobramycin, mirroring what is done clinically. The peg-lid was briefly washed in DPBS to remove non-adherent cells and transferred to a treatment plate and incubated at 35° C. for 8-hrs. At 0, 2, 4, 6, and 8-hrs pegs were collected and BacTiter-Glo™ was used to determine cell viability.

Results

Figure 2:
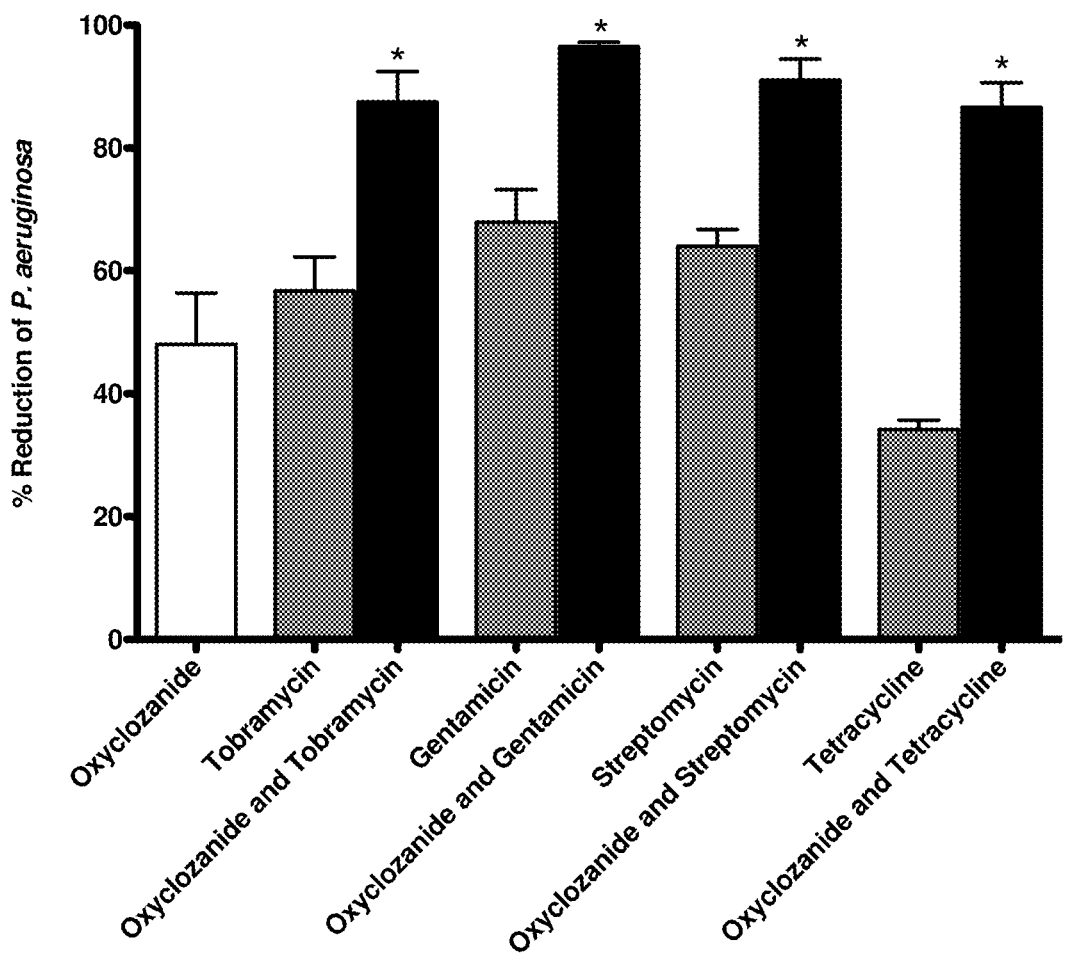
FIG. 2 shows oxyclozanide and tobramycin synergize to kill 24-hr old biofilms. 24-hr old biofilms grown on MBEC plates were treated for 6-hrs with oxyclozanide (100 μM), or tobramycin (500 μM), or gentamicin (100 μM), streptomycin (100 μM), or tetracycline (100 μM), alone and in combination, and the number of viable cells within the biofilms were quantified by BacTiter-Glo™. The assay was performed at least three times in triplicate. The results represent means plus the standard error of the mean (SEM). A one-way ANOVA followed by Bonferroni's multiple comparison post-hoc test was used to determine statistical significance compared to each antibiotic alone (*, $p<0.05$).

Oxyclozanide and Tobramycin Synergize to Kill *P. aeruginosa* Cells within Biofilms In a previous study, we performed a HTS to identify compounds that increased tobramycin efficacy against *P. aeruginosa* biofilms. From this HTS screen, we identified oxyclozanide, which is a halogenated salicylanilide developed for veterinary use against parasitic worm infections (FIG. 1). To confirm the results of the screen, 24-hr old PAO1 biofilms were exposed to 100 µM oxyclozanide or 500 µM (500×MIC) tobramycin alone and in combination for 6-hrs, and the efficacy was determined using BacTiter-Glo™. Oxyclozanide was able to kill 44% of the *P. aeruginosa* in the biofilm, demonstrating it possess some antibacterial activity on its own as recently demonstrated with methicillin resistance *S. aureus*. Similarly, tobramycin killed 56% of the cells at 6-hrs, indicating that either treatment alone had about 2-fold fewer viable cells than the untreated biofilm. However, the combination of oxyclozanide and tobramycin was more effective eradicating 87% (7.7-fold reduction) of the *P. aeruginosa* (FIG. 2). Oxyclozanide combined with the aminoglycosides gentamicin or streptomycin killed 96% (25-fold reduction) or 91% (11.1 fold reduction) of the cells in the biofilm, respectively. Additionally, oxyclozanide also synergized with tetracycline with the combination killing 86% (7.1-fold reduction) of *P. aeruginosa* in a biofilm.

Figure 3:
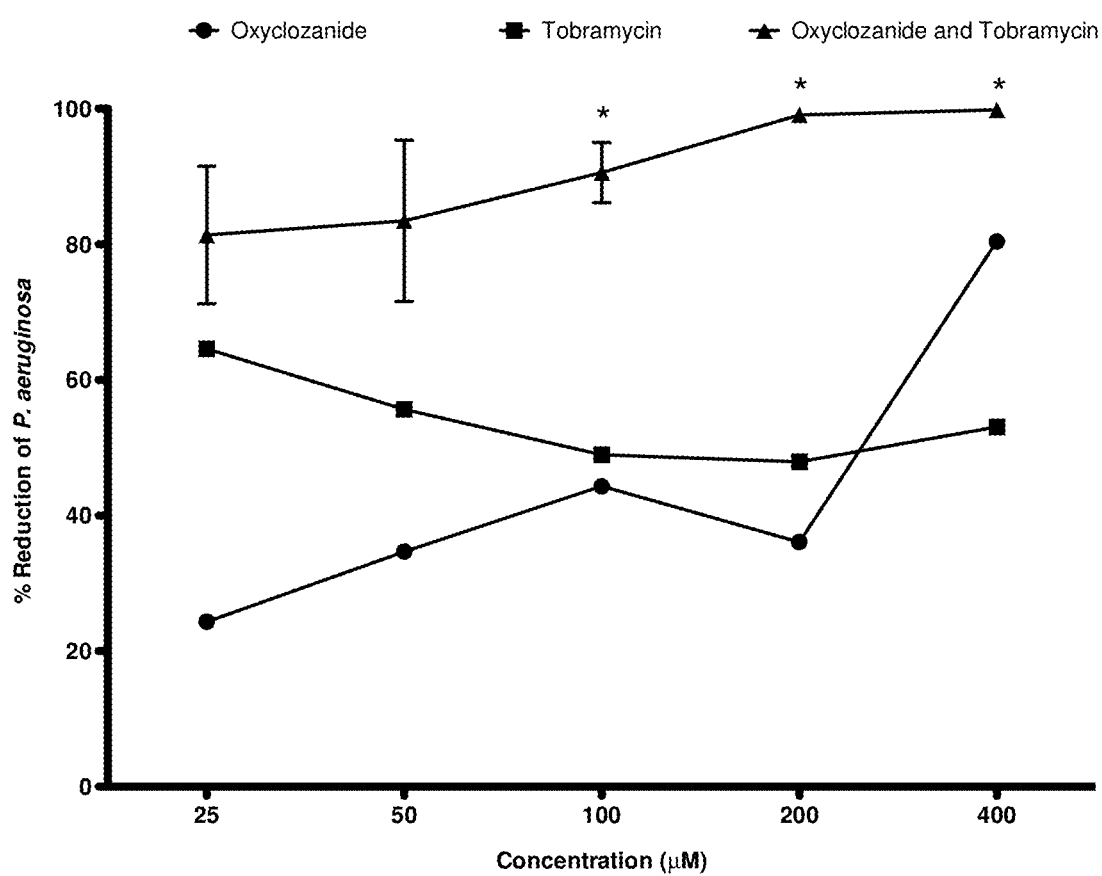
FIG. 3 shows oxyclozanide and tobramycin synergize at multiple concentrations. 24-hr old biofilms grown on MBEC plates were treated for 6-hrs with 2-fold dilutions of equal concentrations of oxyclozanide combined with tobramycin, and the number of viable cells within the biofilms were quantified by the BacTiter-Glo™ assay. The assay was performed at least three times in triplicate. The results represent means plus the SEM. A one-way ANOVA followed by Bonferroni's multiple comparison post-hoc test was used to determine statistical significance compared to tobramycin alone (*, p<0.05).

It was investigated if the synergistic activity observed was specific to biofilm-growing cells. To test this, minimum inhibitory concentration assays were performed on planktonically grown cells. Interestingly, oxyclozanide had no effect on the minimum inhibitory concentration of tobramycin, gentamicin, streptomycin, or tetracycline suggesting that this combination is only effective against cells growing in a biofilm. Oxyclozanide and tobramycin synergize at multiple concentrations Dose response curves were generated to characterize the concentrations of oxyclozanide and tobramycin that were effective at killing biofilms. First, we equally increased twofold serial dilutions the concentration of oxyclozanide and tobramycin alone or in combination from 25 to 400 µM and measured biofilm killing. Tobramycin showed modest activity at concentrations between 25 and 400 µM, reducing the number of the cells within 24-hr old biofilms by between 50 and 60% after 6-hrs of treatment (FIG. 3). Similarly, oxyclozanide exhibited modest activity between 25 and 200 µM, killing approximately 20-40% of the cells within 24-hr biofilms, but at 400 µM, oxyclozanide alone killed ~80% of the cells within 24-hr biofilms. It was found that the combination of oxyclozanide and tobramycin significantly increased killing of biofilms compared with tobramycin treatment alone between 100 and 400 µM, with maximum efficacy seen at 200 µM of oxyclozanide and tobramycin, killing of 99% (100-fold reduction) of the cells within 24-hr biofilms.

Similar dose response curves were also performed with gentamicin, streptomycin and tetracycline either alone or in combination with oxyclozanide ranging from 25 to 400 µM (Fig S1). The combination of oxyclozanide and gentamicin significantly increased killing versus gentamicin alone between 200 and 400 µM (Fig S1A). At these concentrations, gentamicin was less effective. Maximal efficacy was seen at 400 µM, killing 99% of the cells within the biofilm. Alternatively, the combination of oxyclozanide and streptomycin was less effective with significant killing versus streptomycin alone only observed at 200 (80%) and 400 µM (99%), (Fig S1B). The combination of oxyclozanide and tetracycline significantly increased killing between 100 and 400 µM (Supplemental FIG. 1C). Maximal efficacy was seen at 200 µM, killing 97% of the cells in the biofilm.

Figure 4:
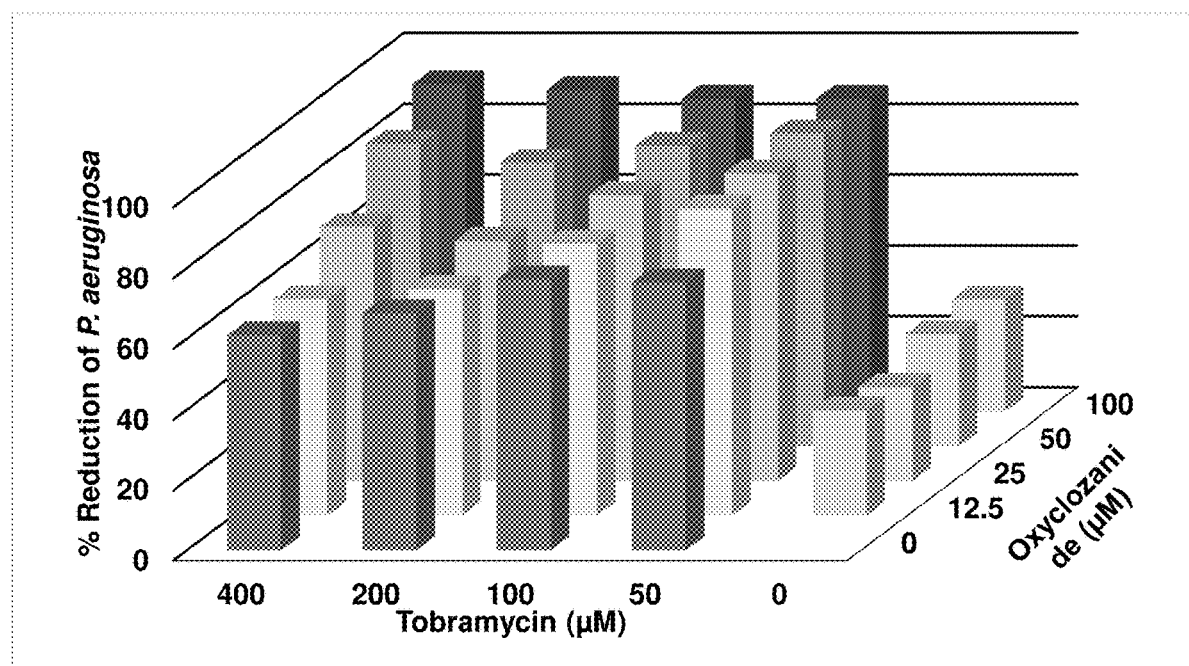
FIG. 4 shows oxyclozanide enhances high concentrations of tobramycin. 24-hr old biofilms grown on MBEC plates were treated for 6-hrs with checkerboard dilutions of oxyclozanide combined with tobramycin. Number of viable cells within the biofilms were quantified by BacTiter-Glo™. The assay was performed two times in triplicate. The results represent means.

Checkerboard experiments varying the concentration of one compound while holding the other constant were preformed to determine the lowest possible combinations of oxyclozanide and tobramycin that resulted in significant killing (FIG. 4). Biofilms were treated with dilutions of oxyclozanide, ranging from 12.5 to 100 µM, and tobramycin, ranging from 50 to 400 µM. 50 or 100 µM of oxyclozanide combined with tobramycin at any concentration tested resulted in 80-90% killing, respectively. These data indicate that relatively low concentrations of oxyclozanide are needed for the combination to be effective.

Figure 5:
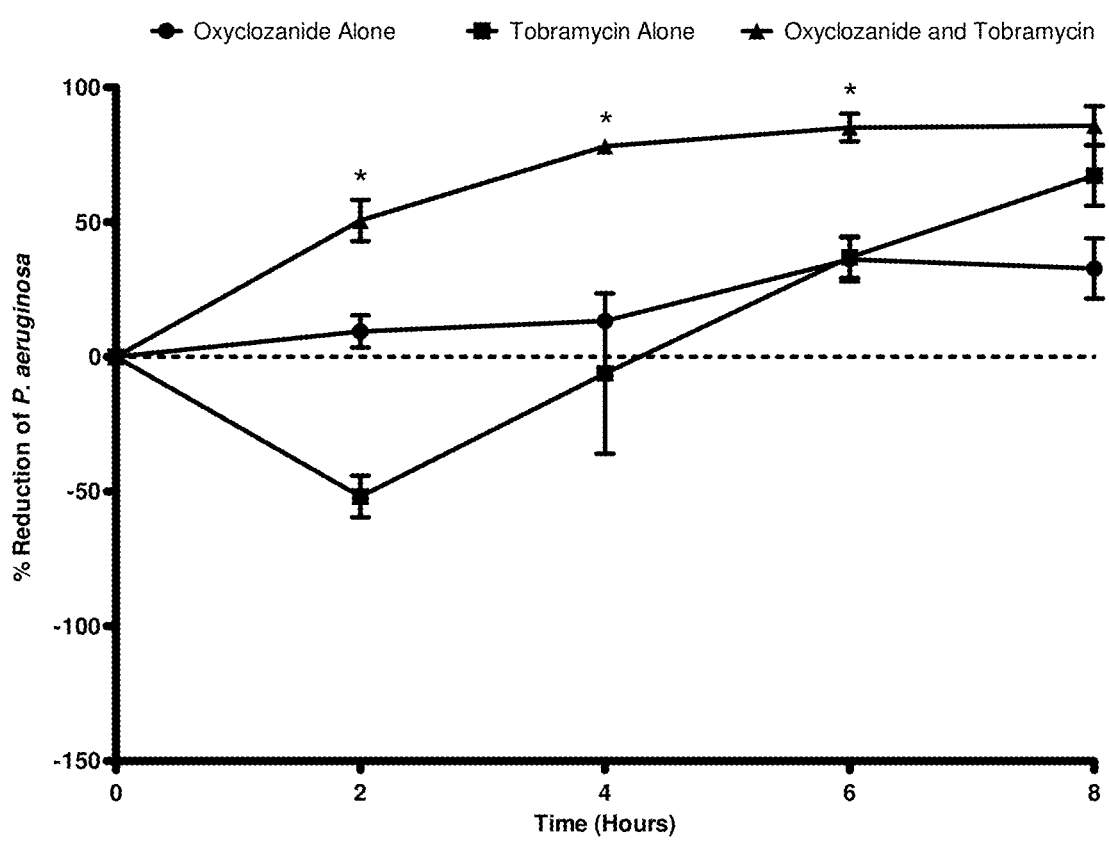
FIG. 5 shows oxyclozanide enhances the onset and maximum efficacy of tobramycin. 24-hr old biofilms grown on MBEC plates were treated with oxyclozanide (100 μM), or tobramycin (500 μM), alone and in combination. At 0, 2, 4, 6, and 8-hrs the number of viable cells within the biofilms were determined by BacTiter-Glo™. The assay was performed at least three times in triplicate. The results represent means plus the SEM. A one-way ANOVA followed by Bonferroni's multiple comparison post-hoc test was used to determine statistical significance compared to tobramycin alone (*, p<0.05).

Oxyclozanide Combined with Tobramycin Accelerates the Killing of Cells within Biofilms Tobramycin treatment of *P. aeruginosa* biofilms initially results in increased biofilm formation at 2 hours followed by slow killing over time. To determine if similar dynamics occurred with the combination or oxyclozanide with tobramycin, the percent killing of *P. aeruginosa* biofilms by 100 mM oxyclozanide or 500 mM tobramycin alone or in combination over the course of 8-hrs was calculated. Our results indicate that oxyclozanide significantly shortened the onset of action of tobramycin from 6-hrs to 2-hrs (FIG. 5), resulting in 57%, 76%, and 80% killing of the cells within the biofilm at 2, 4, and 6 hrs, respectively. Conversely, tobramycin treatment alone led to an increase in cell number between 2-hrs and 4-hrs, rather than cell death. This observation may be due to bacterial stress response initiated by antimicrobial toxicity. Likewise, oxyclozanide alone exhibited no significant killing at 2 and 4 hours. Thus, at two hours the combination of oxyclozanide and tobramycin was 100-fold more effective at killing biofilms than tobramycin treatment alone, indicating this combination exhibits both enhanced activity and accelerated action.

In addition, oxyclozanide significantly accelerated the onset of action of gentamicin from 4-hrs to 2-hrs (Fig S2A). And oxyclozanide enhanced the activity of gentamicin at 2, 4 and 6-hrs. Conversely, unlike the other aminoglycosides examined, streptomycin did not show a delay in killing activity against biofilms (Fig S2B), and we observed minimal enhancement when combined with oxyclozanide only at 6-hrs. Similarly, tetracycline did not show a delay in activity against 24-hr old biofilms (Fig S2C). However, oxyclozanide significantly enhanced tetracycline activity at 2, 4 6, and 8-hrs.

Oxyclozanide Combined with Tobramycin does not Increase Biofilm Dispersal

Figure 6:
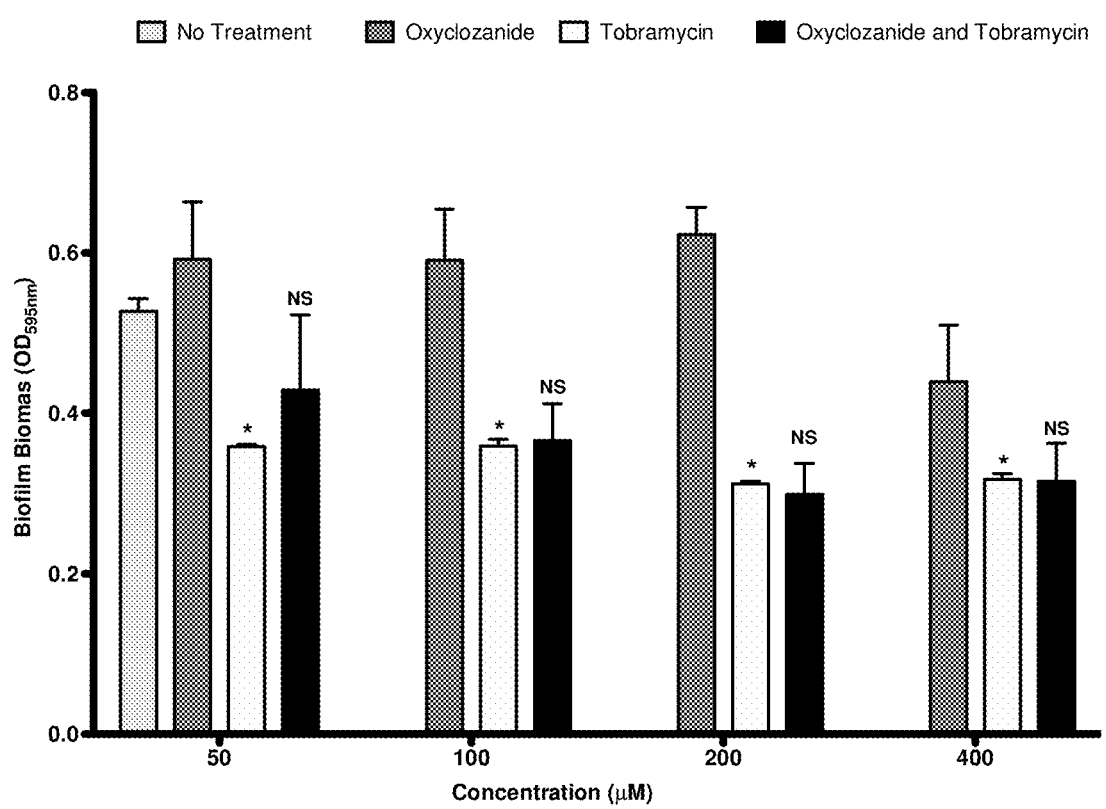
FIG. 6 shows oxyclozanide combined with tobramycin does not increase biofilm dispersal. 24-hr old biofilms grown on MBEC plates were treated with oxyclozanide (100 μM), or tobramycin (500 μM), alone and in combination. The effect on biofilm biomass was quantified by staining with crystal violet. The experiment was performed twice in triplicate. The results represent the means plus SEM. A one-way ANOVA followed by Dunnett's multiple comparison post-hoc test was used to determine statistical significance compared to no treatment and compared to tobramycin alone (*, p<0.05, NS, not significant).

One possible mechanism by which oxyclozanide enhances tobramycin activity is by inducing biofilm dispersal. To test this, the ability of oxyclozanide and tobramycin to disperse P. aeruginosa biofilms was examined using crystal violet staining of the biofilm biomass after six hour exposure to dilutions of oxyclozanide or tobramycin alone and in combination from 50 µM-400 µM (FIG. 6). As we have previously observed, tobramycin treatment alone significantly reduced biofilm biomass at all concentrations examined. Conversely, oxyclozanide did not impact biofilm biomass. However, at no concentration did oxyclozanide enhance tobramycin dispersal of the biofilm compared to tobramycin treatment alone. This suggest the combination enhances the killing of cells within the biofilm rather than causing biofilm dispersal.

Oxyclozanide and Tobramycin are Effective Against Clinical Isolates from CF Patients P. aeruginosa can evolve to a variety of different morphotypes in the lungs of CF patients, and thus any treatment for CF should be widely effective against these different strains. To determine if the combination of oxyclozanide and tobramycin exhibited widespread activity, its activity was tested against six clinical isolates from patients enrolled at the MSU CF Clinic or University of Washington. Two clinical isolates were isoalted longitudinally from the same patient at 6 months of age and 8 years of age: AMT0023-30 and 34, respectively. In addition, clinical isolates CF_110_N and CF_110_O were isolated longitudinally from the same patient 3 months apart (Table 1). Using isolates collected from the same patient at different times allowed us to test the activity of oxyclozanide and tobramycin against P. aeruginosa in a chronic infectious state.

Figure 7:
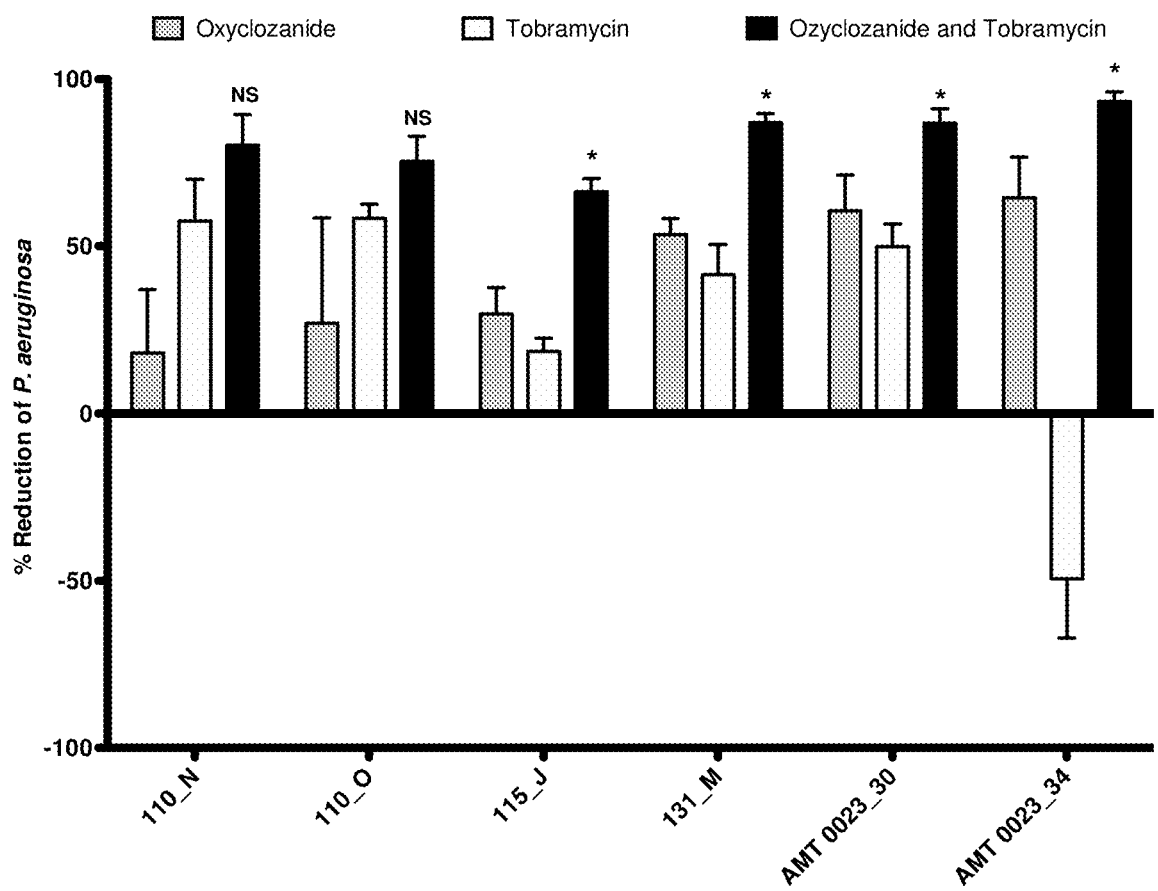
FIG. 7 shows Tobramycin and oxyclozanide are effective against clinical isolates. 24-hr old biofilms grown on MBEC plates were treated with oxyclozanide (100 μM), or tobramycin (500 μM), alone and in combination for 6-hrs. The number of viable cells within the biofilms were quantified by BacTiter-Glo™. The assay was performed three times in triplicate. The results represent means plus the SEM. A one-way ANOVA followed by Bonferroni's multiple comparison post-hoc test was used to determine statistical significance compared to tobramycin alone (*, p<0.05, NS, not significant).
Figure 8:
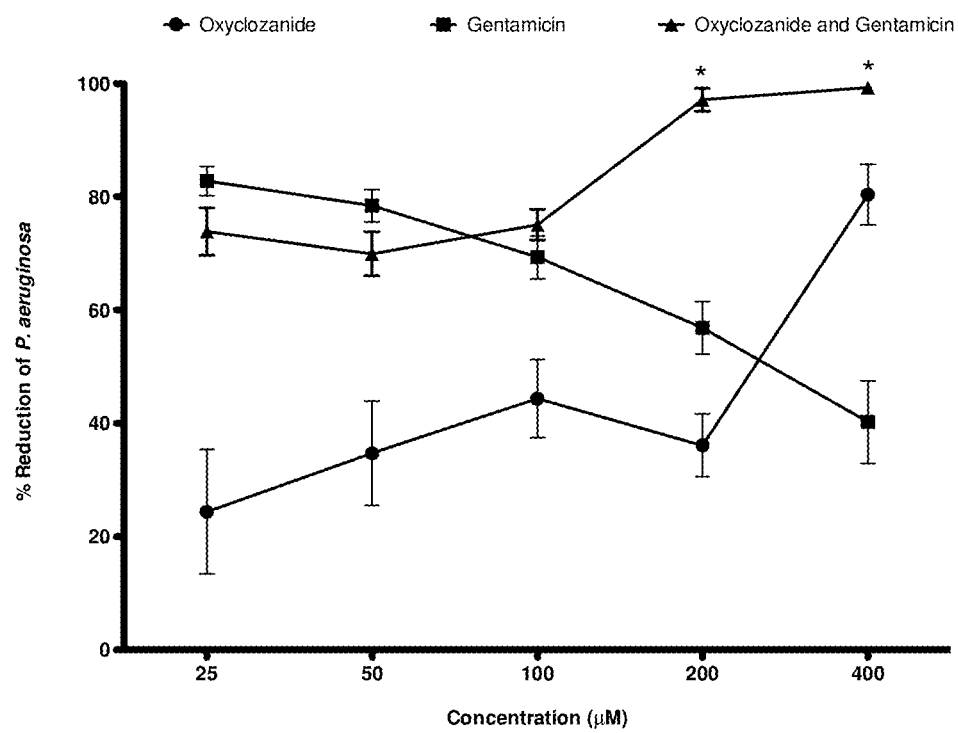
FIG. 8 shows oxyclozanide and gentamicin, streptomycin, or tetracycline synergize at multiple concentrations. 24-hr old biofilms grown on MBEC plates were treated for 6-hrs with 2-fold dilutions of equal concentrations of oxyclozanide combined with gentamicin, streptomycin, or tetracycline. The number of viable cells within the biofilms were quantified by BacTiter-Glo™. The assay was performed at least three times in triplicate. The results represent means plus the SEM.
Figure 8:
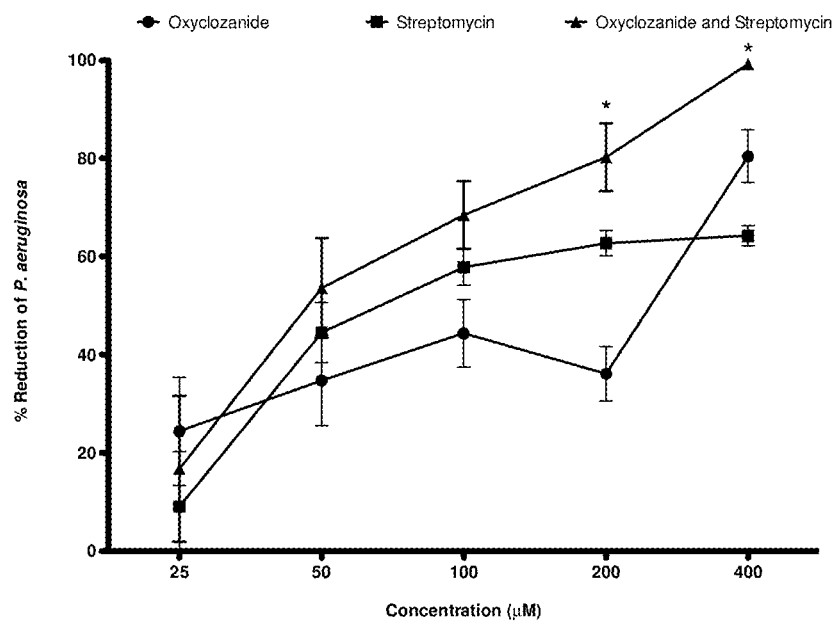
Figure 8:
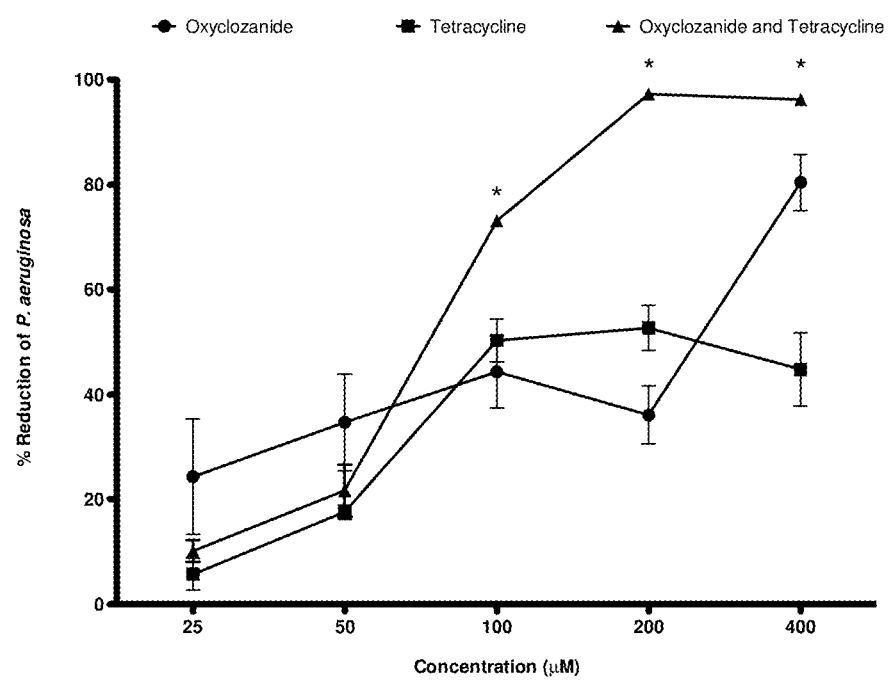
Figure 9:
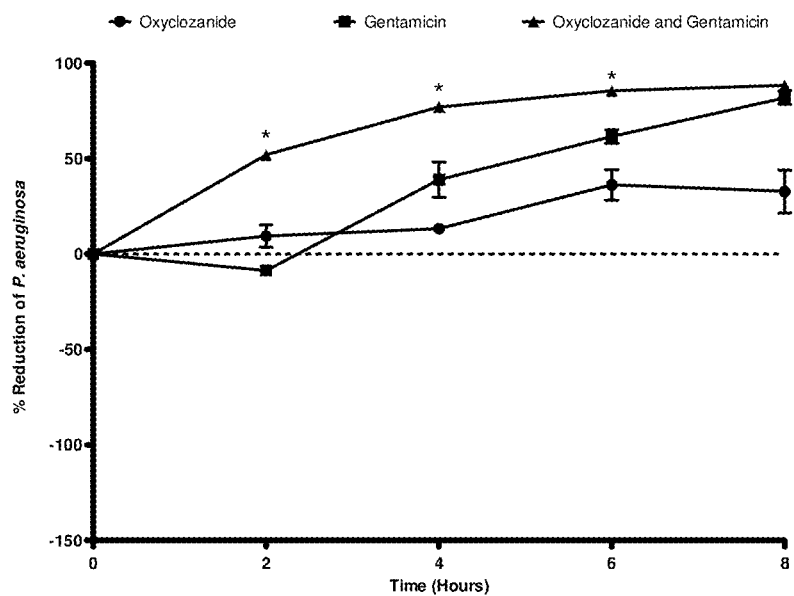
FIG. 9 shows gentamicin and tetracycline have a shorter onset of action and enhanced killing when combined with oxyclozanide. 24-hr old biofilms grown on MBEC plates were treated with oxyclozanide (100 μM), gentamicin (100 μM), streptomycin (100 μM), or tetracycline (100 μM) alone and in combination for 8-hrs. At 0, 2, 4, 6, and 8-hrs the number of cells within the biofilms were determined using BacTiter-Glo™. The assay was performed at least three times in triplicate. The results represent means plus the SEM.
Figure 9:
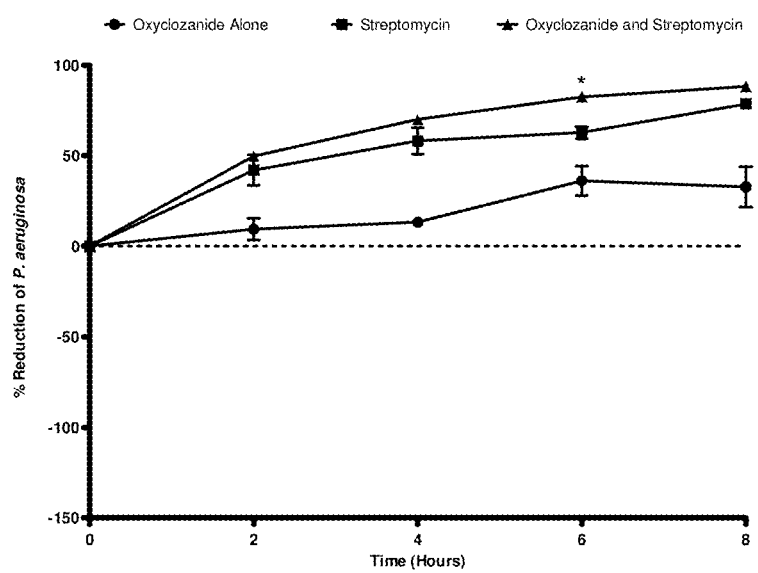
Figure 9:
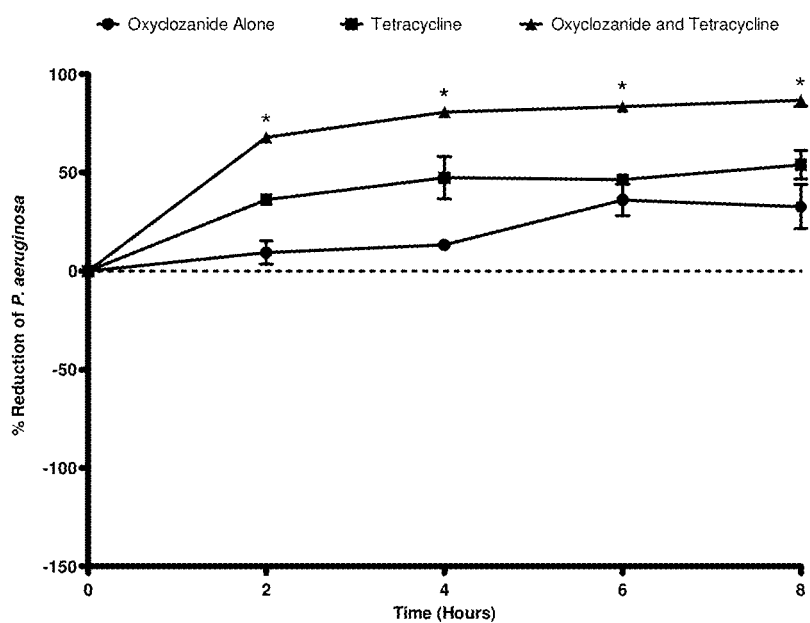
Figure 10:
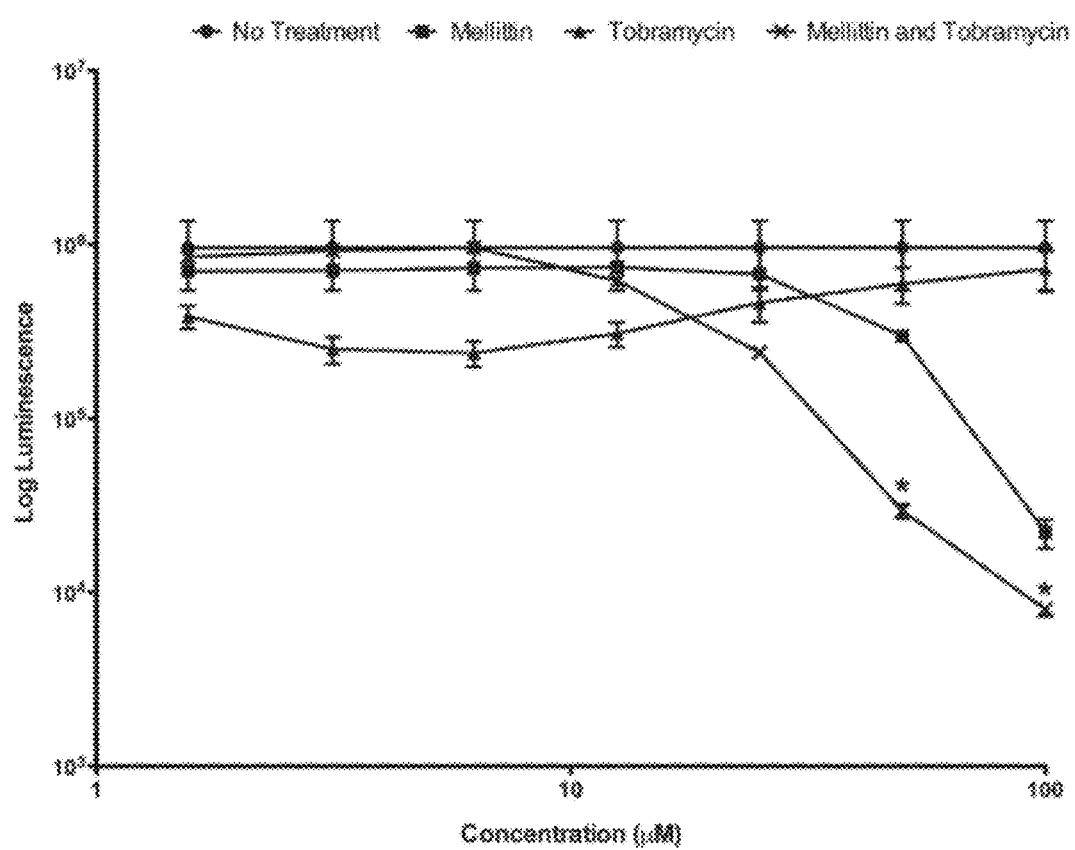
FIG. 10 shows melittin is effective alone and enhances tobramycin against *P. aeruginosa* biofilms. 24-hr biofilms were treated with melittin or tobramycin alone and in combination in two-fold dilutions. The number of viable cells was quantified using BacTiter-Glo™. The assay was performed two times in triplicate. The results represent means plus SEM. A two-way ANOVA was performed followed by a Tukey's multiple comparisons test to determine statistical significance between tobramycin and the combination (*, p<0.05).
Figure 11:
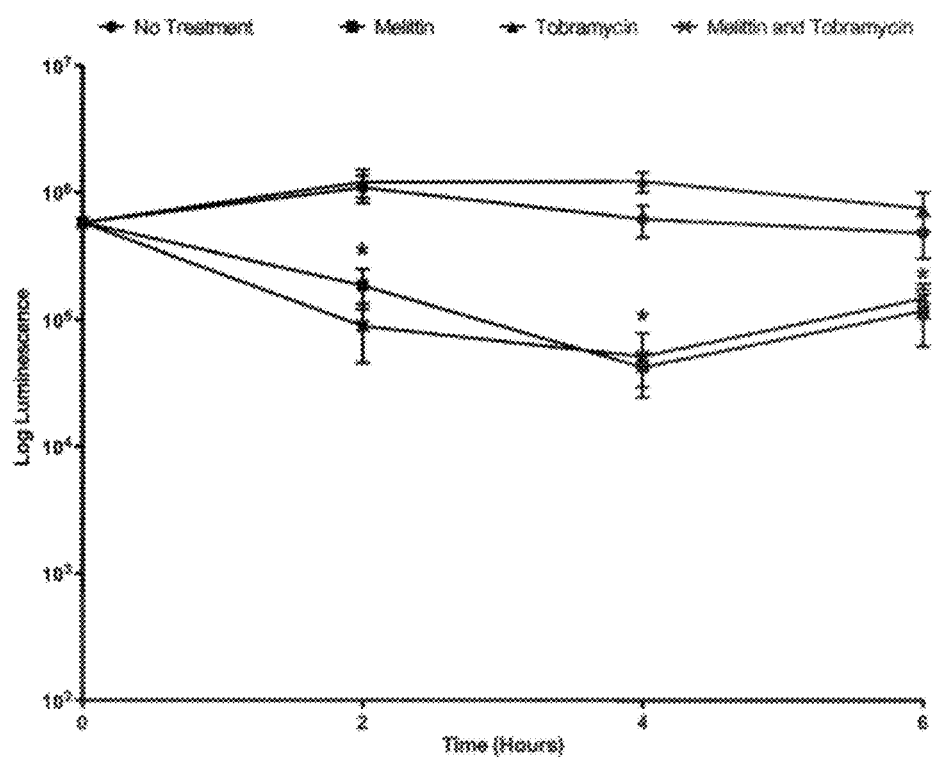
FIG. 11 shows melittin has a shorter onset of action than tobramycin. 24-hr old biofilms grown on MBEC™ plates were treated with melittin (100 μM) or tobramycin (400 μM) alone and in combination. At 0, 2, 4, and 6-hrs the number of viable cells within the biofilms were determined by BacTiter-Gio™. The assay was performed two times in triplicate. The results represent means plus/minus SEM. A two-way ANOVA was performed followed by a Tukey's multiple comparisons test to determine statistical significance between tobramycin and the combination(*, p<0.05. NS, not significant).
Figure 12:
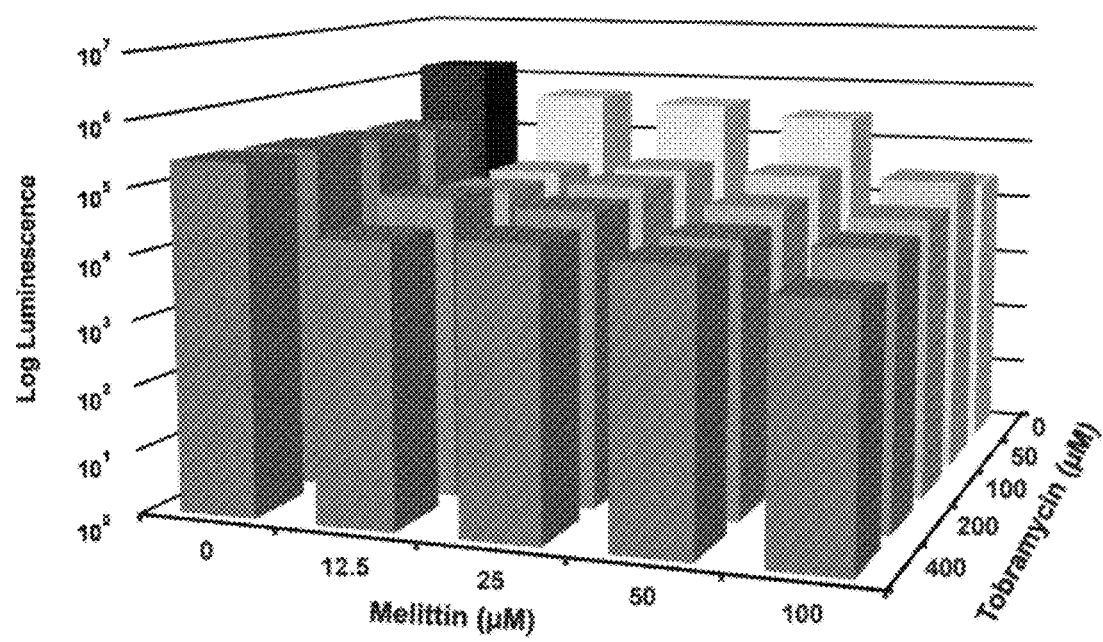
FIG. 12 shows that melittin and tobramycin are effective at micromolar concentrations. 24-hr old biofilms grown on MBEC™ plates were treated for 6-hrs with checkerboard dilutions of melittin combined with tobramycin. Number of viable cells within the biofilms were quantified by BacTiter-Gio™. The assay was performed two times in triplicate. The results represent means.
Figure 13:
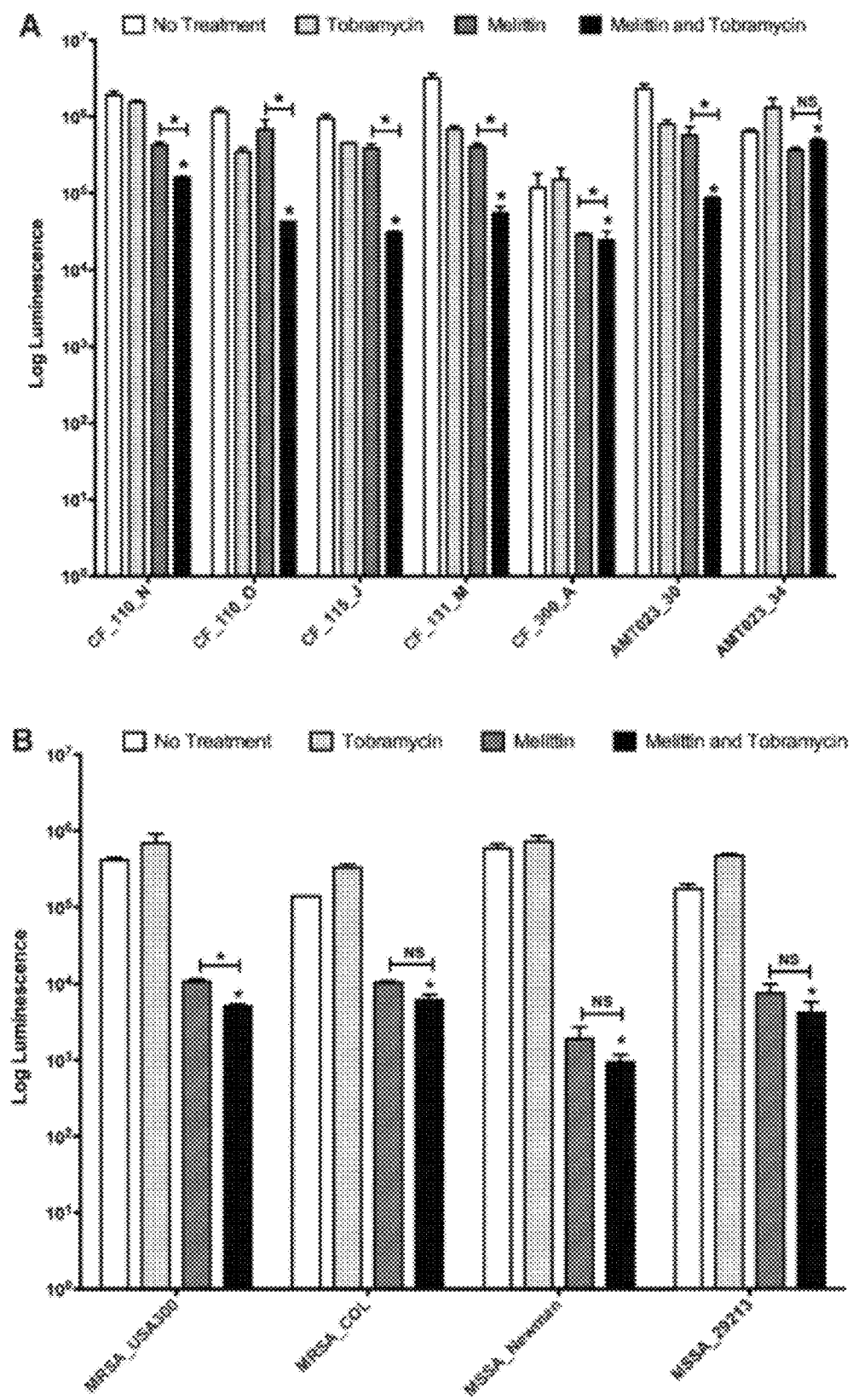
FIG. 13 has two panels, A and B, and shows that melittin is effective in combination with tobramycin against *P. aeruginosa* and *S. aureus* biofilms. Panel A shows 24-hr old *P. aeruginosa* were treated with melittin (50 μM) or tobramycin (400 μM) alone and in combination. Part B shows that 24-hr old *S. aureus* biofilms were treated with melittin (100 μM) or tobramycin (100 μM) alone and in combination. The number of viable cells was quantified using BacTiter-Gio™. The assay was performed twice in triplicate. The results represent means plus SEM. A two-way ANOVA was performed followed by a Tukey's Multiple Comparisons Test to determine statistical significance between tobramycin and the combination and between melittin and the combination (*, p<0.05, NS, not significant).
Figure 14:
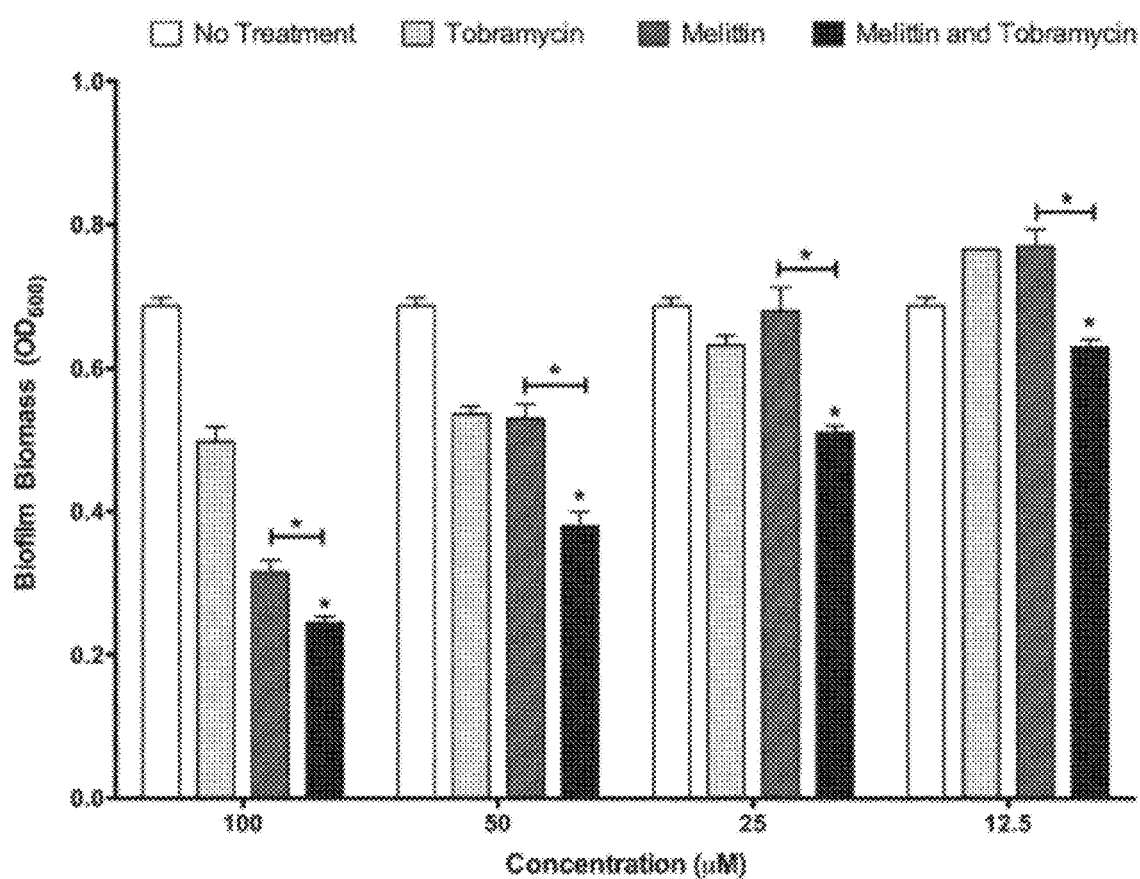
FIG. 14 shows melittin causes biofilm dispersal alone and in combination with tobramycin. 24-hr biofilms were treated for 6-hrs and biofilm dispersal was quantified using crystal violet staining. The assay was performed at least four times in triplicate. The results represent means plus SEM. A two-way ANOVA was performed followed by a Tukey's Multiple Comparisons Test to determine statistical significance between tobramycin and the combination and between melittin and the combination(*, p<0.05).
Figure 15:
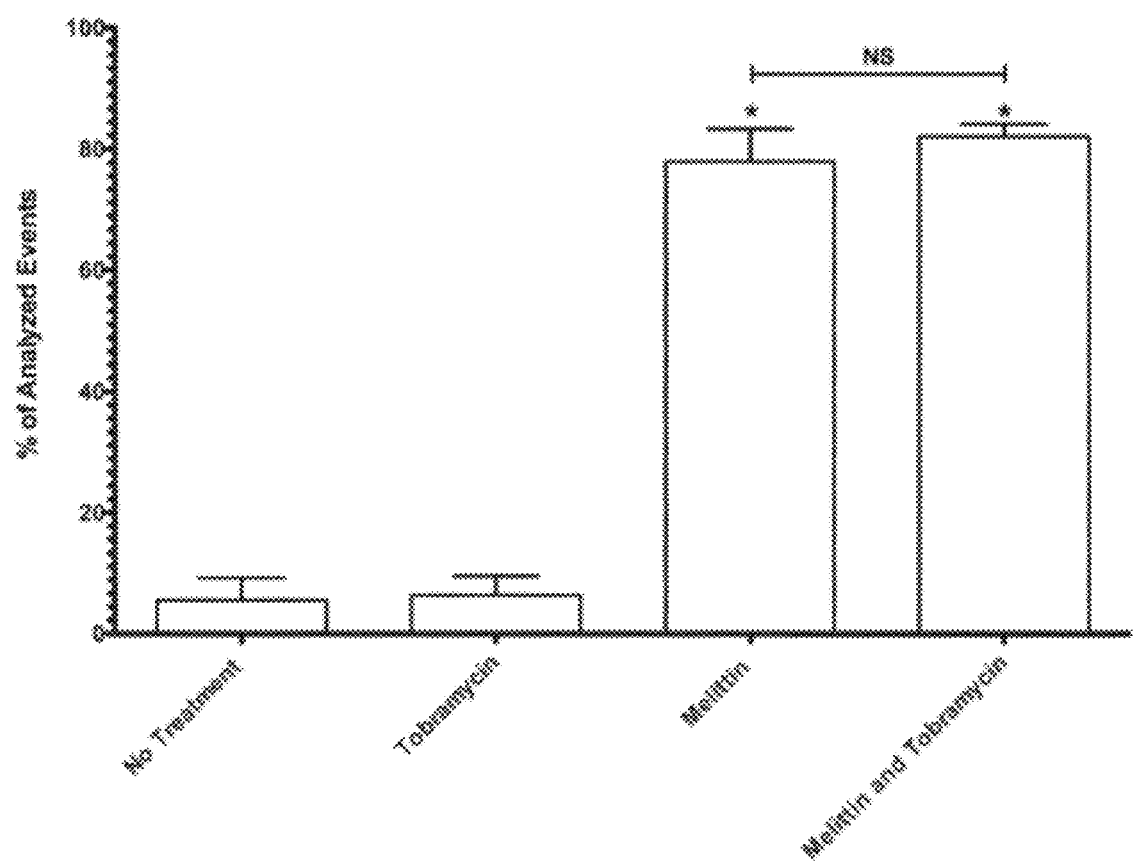
FIG. 15 shows melittin causes permeabilization of *P. aeruginosa* cells within biofilms. 24-hr old biofilms were treated with melittin (100 μM), or tobramycin (400 μM), alone and in combination for 2 hours. Panel A shows cells were stained with TO-PRO-3 to determine the number of cells that were permeabilized. Percent values indicate the average relative abundance of events within each gate normalized to the total number of events analyzed, excluding artifacts, aggregates and debris. The experiment was performed two separate times in duplicate. The results are percent averages plus the SEM. A one-way ANOVA followed by Bonferroni's multiple comparison post-hoc test was used to determine statistical significance between tobramycin versus melittin, tobramycin versus the combination, and melittin versus the combination(*, p<0.05).
Figure 16:
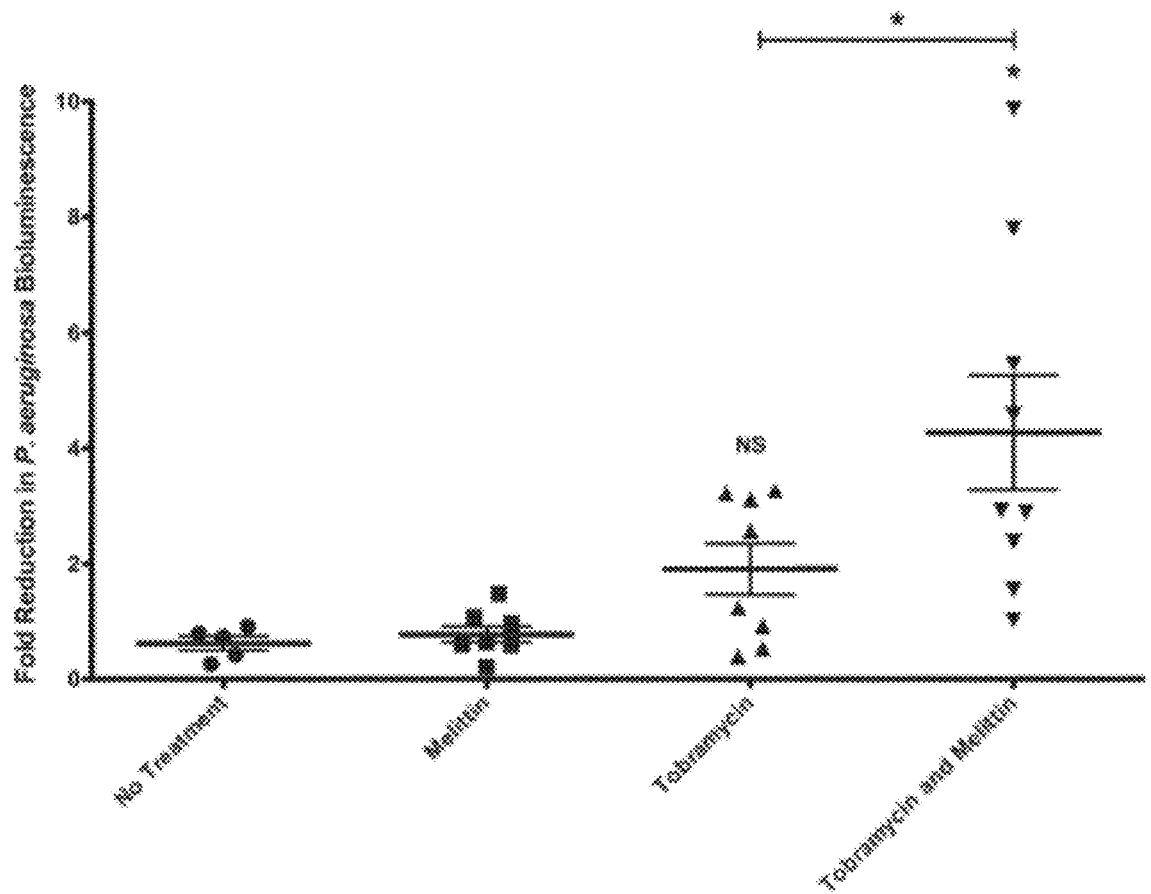
FIG. 16 shows melittin and tobramycin are more effective than tobramycin alone against *P. aeruginosa* biofilms using a murine wound model. 24-hr old bioluminescent biofilms formed within wounds were treated with melittin (100 µM), or tobramycin (400 µM), alone and in combination for 4-hrs. Reduction in the number of cells within biofilms was quantified using IVIS. The results are fold reduction of two separate experiments±the SEM, no treatment n=5, melittin n=8, tobramycin n=8, melittin and tobramycin n=9. A one-way ANOVA followed by Bonferroni's multiple comparison post-hoc test was used to determine statistical significance between each treatment and the untreated control and tobramycin treatment alone was compared with tobramycin and melittin (*, p<0.05, NS, not significant).
Figure 17:
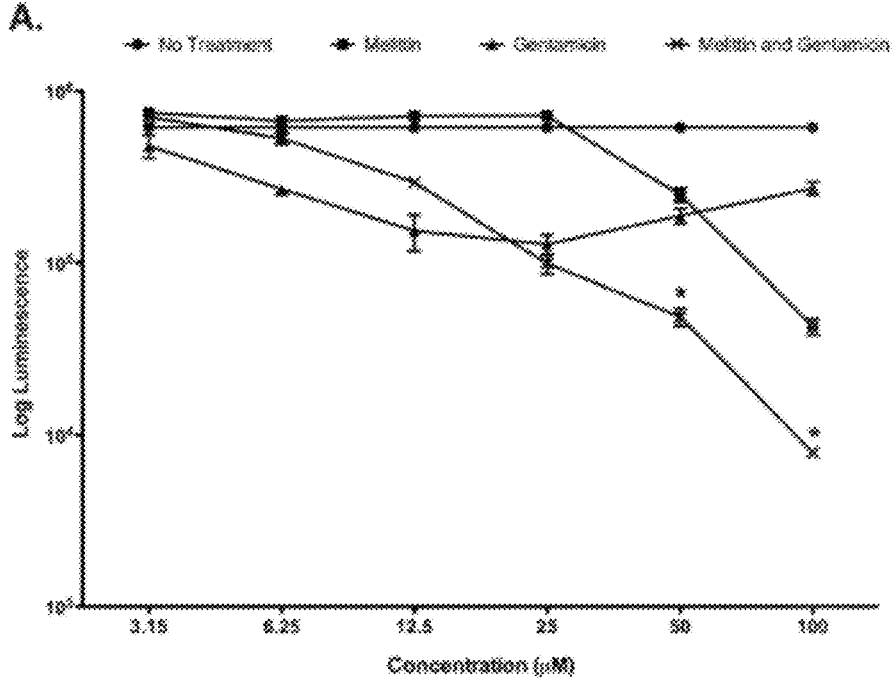
FIG. 17 has two panels, A and B, and shows melittin in combination with gentamicin or streptomycin is effective against *P. aeruginosa* biofilms. 24-hr biofilms were treated with melittin or (Panel A) gentamicin or (Panel B) streptomycin in two-fold dilutions. The number of viable cells was quantified using BacTiter-Gio™. Melittin and no treatment were re-plotted in each figure for comparison. The assay was performed once in triplicate. The results represent means plus/minus SEM. A two-way ANOVA was performed followed by a Tukey's Multiple Comparisons Test to determine statistical significance (Panel A) between gentamicin and the combination and (Panel B) between streptomycin and the combination(*, p<0.05. NS, not significant).
Figure 17:
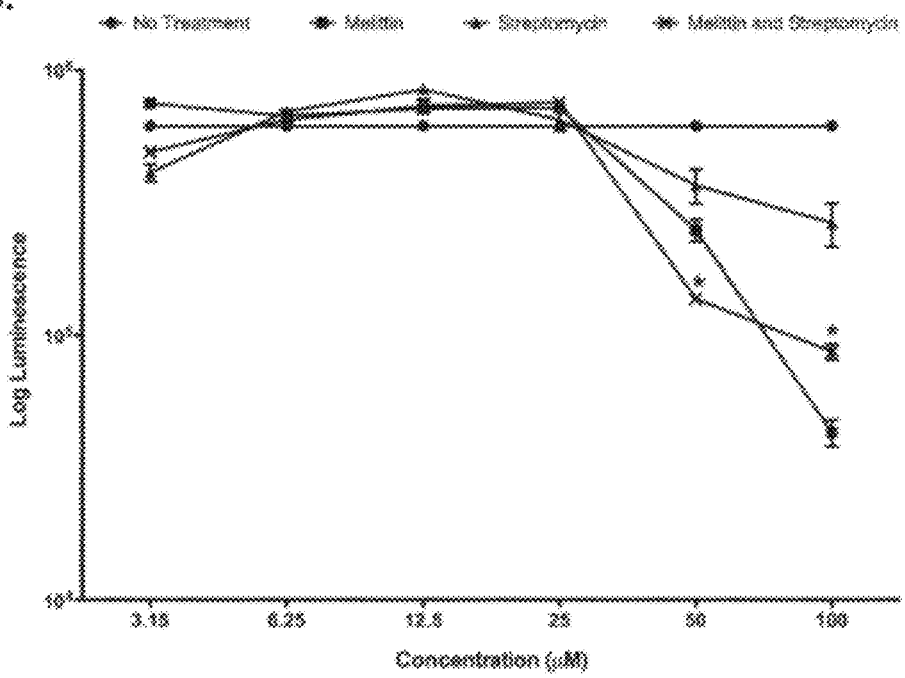
Figure 18:
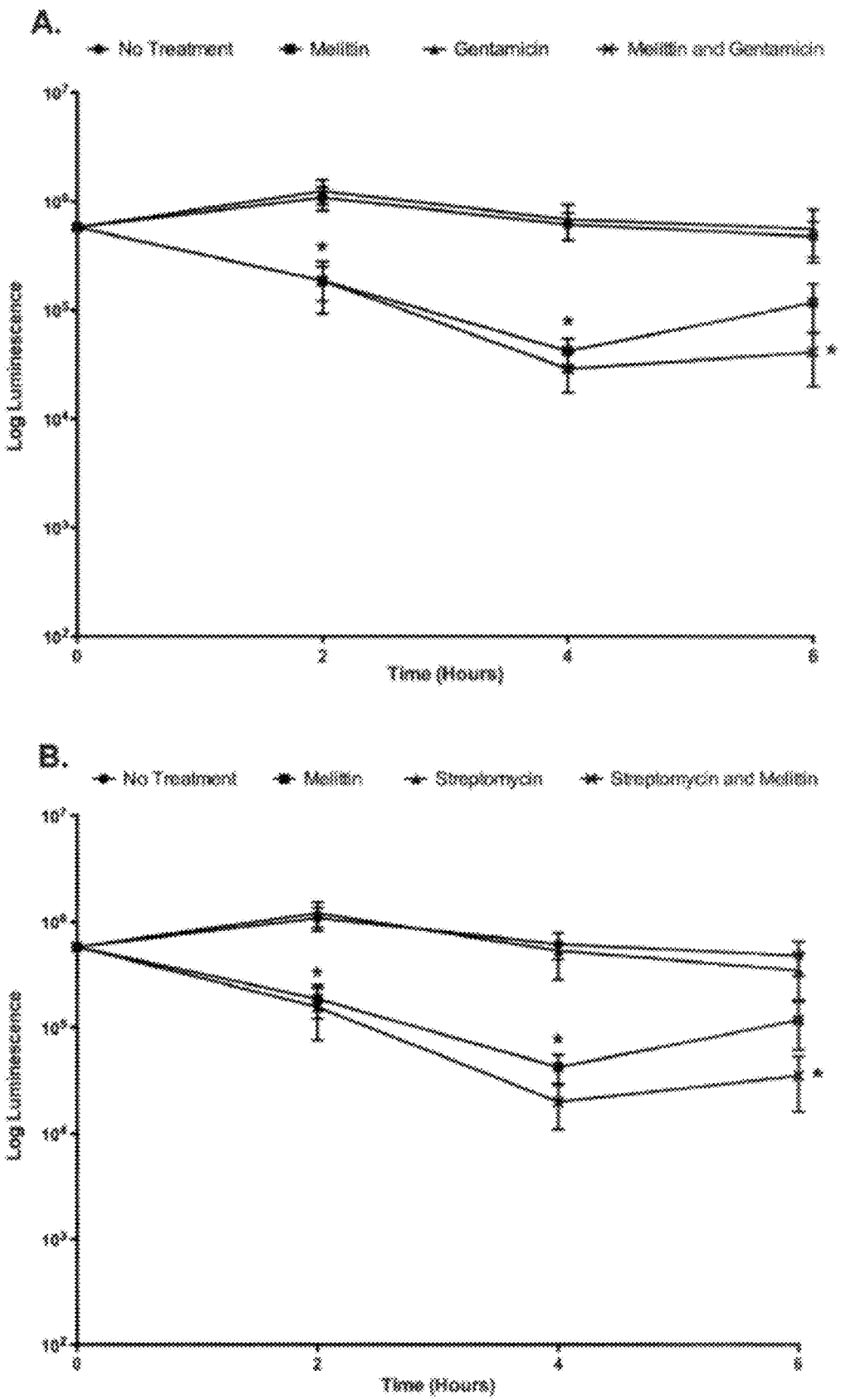
FIG. 18 has two panels, A and B, and shows that melittin has a shorter onset of action than gentamicin or streptomycin. 24-hr old biofilms grown on MBEC™ plates were treated with melittin (1 00 ~M) or (Panel A) gentamicin (100 µM) or (Panel B) streptomycin (1 00 µM) in combination. At 0, 2, 4, and 6-hrs the number of viable cells within the biofilms were determined by BacTiter-Gio™. The assay was performed two times in triplicate. Melittin and no treatment were re-plotted in each figure for comparison. A two-way ANOVA was performed followed by a Tukey's Multiple Comparisons Test to determine statistical significance between gentamicin and the combination and between streptomycin and the combination(*, p<0.05. NS, not significant)
.

These six clinical isolates were treated with 100 µM oxyclozanide or 500 µM alone or in combination. Like PA01, all six isolates exhibited modest sensitivity to oxyclozanide treatment alone. The combination enhanced killing of all of these P. aeruginosa clinical isolates grown in biofilms compared with tobramycin treatment alone, and the increased killing of 4/6 clinical isolates was found to be statistically significant (FIG. 7). Importantly, this combination significantly enhanced killing of a tobramycin resistant strain, AMT0023-34. This strain over expresses the MexXY-OpRM multidrug pump, rendering it resistant to tobramycin. The combination resulted in a 300-fold reduction in viable AMT0023-34 compared with tobramycin alone.

Discussion

The antibiotic arsenal has decreased with each passing decade due to the emergence of MDR bacteria and a lack of research and development by major pharmaceutical companies. Drug repurposing affords many benefits, including reduced costs and accelerated deployment, making it an attractive strategy for the development of new therapies for bacterial infections. FDA approved salicylanilide anthelmintic drug, oxyclozanide, enhances the activity of an aminoglycosides and tetracycline against the opportunistic pathogen P. aeruginosa.

Recently, it has been found that the anthelmintics, niclosamide and oxyclozanide, demonstrate activity against Gram-positive methicillin resistant Staphylococcus aureus. Young CF patients are often colonized with Gram-positive Staphylococcus organisms, making tobramycin combined with oxyclozanide an applicable therapy for both early and late CF lung pathogens. Importantly, this combination therapy may have activity against both Gram-negative and Gram-positive pathogens. P. aeruginosa is also responsible for non-healing chronic wounds such as diabetic foot ulcers and burns. Oxyclozanide combined with tobramycin might more effectively treat these infections. We are currently evaluating if oxyclozanide possesses the ability to enhance aminoglycosides and tetracycline activity against additional members of MDR "ESKAPE" organisms.

The mechanism of action of oxyclozanide, at least in flukes, is thought to be by uncoupling oxidative phosphorylation by acting as a proton ionophore. If this same mechanism occurs in bacteria, this would result in the collapse of the proton motive force (PMF) required for ATP synthesis and the efflux of toxic compounds by efflux pumps. It is possible oxyclozanide enhances tobramycin activity by reducing or collapsing the PMF, decreasing the efflux of tobramycin and increasing its accumulation within the cell. Alternatively, oxyclozanide could disrupt the cell membrane of P. aeruginosa enhancing the "self-promoted uptake" of tobramycin. In fact, it has been shown that oxyclozanide permeabilizes Gram-positive bacteria. Whether oxyclozanide enhance tobramycin activity through these mechanisms or others is actively being investigated.

Previously, veterinary drugs such as ivermectin have been successfully repurposed for the treatment of several diseases in humans. Oxyclozanide deserves further study for development as a human antimicrobial. The use of anthelmintics against MDR bacteria could represent a viable solution for the current antibiotic shortage and lead to the enhanced eradication of P. aeruginosa infections in CF patients as well as diabetic foot ulcers and burn wounds.

Tables

TABLE 1

Bacterial Strains

| Strain | Characteristics | Source or Reference |
|---|---|---|
| PAO1 | Wild type reference strain | |
| AMT0023-30 | Early Isolate 6 MO | |
| AMT0023-34 | Late Isolate 8 YO | |
| CF_110_N | Pediatric CF Isolate 3 MO earlier | MSU CF Clinic |
| CF_110_O | Pediatric CF Isolate 3 MO later | MSU CF Clinic |

Another example of an enthelmintic compound that has synergy with aminoglycoside such as tobramycin or gentamicin is melittin, an antimicrobial peptide (FIGS. 10-18). Melittin is one of the main components of bee venom and is hydrophobic except for a region with Lys-Arg-Lys-Arg sequence near C-terminal end. This structural characteristic makes melittin a highly surface-active and able to form holes in the outer membrane of bacteria.

Our studies found a ~2 log reduction in the number of cells within 24-hr P. aeruginosa biofilms with melittin alone, and a 2-3 log reduction when used in combination with tobramycin. Melittin was effective in as little as 2-hrs, whereas, tobramycin required 6-hrs to show antimicrobial activity. Melittin causes significant biofilm dispersal and was more effective than tobramycin. Melittin also showed potent activity against Staph aureus biofilms, resulting in a ~2 log reduction after 6-hrs of treatment. Lower concentrations of melittin and tobramycin exhibit synergy.

Finally, melittin increased the potency of tobramycin, causing a left shift in half effective concentration 50 (EC50)

from 46 µM to 16 µM. The figures also demonstrate synergy between tobramycin and melittin in a mouse wound model infected with *P. aeruginosa* biofilms. Thus, melittin is a powerful antimicrobial agent with activity against *P. aeruginosa* and *Staph aureus*. In addition, melittin both enhanced tobramycin activity and potency when used in combination. Table 1 shows the minimum inhibitory concentrations of anti-microbials.

SUPPLEMENTAL TABLE 1

Minimum Inhibitory Concentrations (MIC)

| Antimicrobial | Alone (µM) | +Melittin (µM) |
|---|---|---|
| Melittin | 62.5-200 | — |
| Tobramycin | 3.125-6.25 | 3.125-6.25 |
| Gentamicin | 6.25-12.5 | 12.5 |
| Streptomycin | 25.0-50.0 | 25.0-50.0 |

MIC were determined as the minimum concentration that no turbidity greater than background was measured.

Table 2 shows melittin enhances micromolar concentrations of tobramycin. 24-hr old biofilms grown on MBEC™ plates were treated for 6-hrs with checkerboard dilutions of melittin combined with tobramycin. Number of viable cells within the biofilms were quantified by BacTiter-Gio™. The assay was performed two times in triplicate. The results represent means plus/minus the Standard Error Deviation. A two-way ANOVA followed by Sidak's multiple comparison was used to determine statistical significance compared to tobramycin treatment alone. Table entries in bold indicate significance (p<0.05) and entries in italics are not significant because melittin is effective alone at these concentrations.

| | Melittin | | | | |
|---|---|---|---|---|---|
| Tobramycin | 100 µM | 50 µM | 25 µM | 12.5 µM | 0 µM |
| 400 µM | 7.96E3 (±7.14E3) | 1.79E4 (±2.28E4) | 2.64E4 (±3.55E4) | 2.16E4 (±2.79E4) | 2.44EE5 (±1.45E5) |
| 200 µM | *1.77E4* (±*1.45E4*) | 1.94E4 (±1.26E4) | 3.95E4 (±4.13E4) | 4.83E4 (±4.74E4) | 2.27E5 (±9.90E4) |
| 100 µM | *2.40E4* (±*1.24E4*) | 2.88E4 (±1.99E4) | 4.94E4 (±4.96E4) | 3.50E4 (±3.65E4) | 1.91E5 (±7.15E4) |
| 50 µM | *5.03E4* (±*5.87E3*) | 5.03E4 (±2.52E4) | 5.23E4 (±3.56E4) | 3.90E4 (±2.49E4) | 1.82E5 (±8.91E4) |
| 0 µM | 2.51E4 (±9.58E3) | 2.87E5 (±3.11E5) | 4.22E5 (±4.82E5) | 5.18E5 (±5.90E5) | 1.61E6 (±1.96E5) |

INCORPORATION BY REFERENCE

The contents of all references, patent applications, patents, and published patent applications, as well as the Figures and the Sequence Listing, cited throughout this application are hereby incorporated by reference.

EQUIVALENTS

Those skilled in the art will recognize, or be able to ascertain using no more than routine experimentation, many equivalents to the specific embodiments of the present invention described herein. Such equivalents are intended to be encompassed by the following claims.

We claim:

1. A method for inhibiting the proliferation, viability, or biofilm-forming activity of biofilm-forming bacteria in a human subject suffering from a respiratory disorder, the method comprising contacting the bacteria with an effective amount of: (i) a first agent and (ii) a salicylanilide or a derivative thereof, to thereby inhibit the proliferation, viability, or biofilm-forming activity of the biofilm-forming bacteria, wherein the first agent is an aminoglycoside or a tetracycline; wherein the aminoglycoside is tobramycin, streptomycin, or gentamicin, and wherein the salicylanilide or derivative thereof is oxyclozanide.

2. A method for treating a respiratory disorder in a human subject who is infected with biofilm-forming bacteria, the method comprising administering to the subject an effective amount of: (i) a first agent and (ii) a salicylanilide or a derivative thereof, to thereby inhibit the proliferation, viability, or biofilm-forming activity of the biofilm-forming bacteria, wherein the first agent is an aminoglycoside or a tetracycline; wherein the aminoglycoside is tobramycin, streptomycin, or gentamicin, and wherein the salicylanilide or derivative thereof is oxyclozanide.

3. The method according to claim 2, wherein the respiratory disorder is cystic fibrosis.

4. The method according to claim 2, wherein the subject: (a) is immunocompromised, (b) has a persistent wound, or (c) has an implant that is infected with the biofilm-forming bacteria.

5. The method according to claim 1, wherein the biofilm-forming bacteria are gram negative or gram positive.

6. The method according to claim 1, wherein the biofilm-forming bacteria are *Actinobacillus actinomycetemcomitans, Acinetobacter baumannii, Bordetella pertussis, Brucella* sp., *Campylobacter* sp., *Capnocytophaga* sp., *Cardiobacterium hominis, Eikenella corrodens, Francisella tularensis, Haemophilus ducreyi, Haemophilus influenzae, Helicobacter pylori, Kingella kingae, Legionella pneumophila, Pasteurella multocida, Citrobacter* sp., *Enterobacter* sp., *Escherichia coli, Klebsiella pneumoniae, Proteus* sp., *Salmonella enteriditis, Salmonella typhi, Serratia marcescens, Shigella* sp., *Yersinia enterocolitica, Yersinia pestis, Neisseria gonorrhoeae, Neisseria meningitidis, Moraxella catarrhalis, Veillonella* sp., *Bacteroides fragilis, Bacteroides* sp., *Prevotella* sp., *Fusobacterium* sp., *Spirillum minus, Aeromonas* sp., *Plesiomonas shigelloides, Vibrio cholerae, Vibrio parahaemolyticus, Vibrio vulnificus, Mycobacterium tuberculosis, Acinetobacter* sp., *Flavobacterium* sp., *Pseudomonas aeruginosa, Burkholderia cepacia, Burkholderia pseudomallei, Xanthomonas maltophilia, Stenotrophomonas maltophila, Staphylococcus aureus, Bacillus* spp., *Clostridium* spp., or *Streptococcus* spp.

7. The method according to claim 1, wherein the biofilm forming bacteria are multi-drug resistant pathogens.

8. The method according to claim 7, wherein the multi-drug resistant pathogen is a multi-drug resistant strain of *Enterococcus faecium, Staphylococcus aureus, Klebsiella pneumoniae, Acinetobacter baumanii, Pseudomonas aeruginosa*, or *Enterobacter* species.

9. The method according to claim 1, wherein the salicylanilide or derivative thereof is contacted to the bacteria or administered as a composition comprising at least 100 µm oxyclozanide.

10. The method according to claim 9, wherein the salicylanilide or derivative thereof is contacted to the bacteria or administered as a composition comprising at least 200 µm oxyclozanide.

11. The method of claim 1, wherein the effective amount of the aminoglycoside is less than the amount of the aminoglycoside required for the same level of effectiveness in the absence of salicylanilide or a derivative thereof.

12. The method of claim 1, wherein the effective amount of the aminoglycoside is less than or equal to 90% of the amount of the aminoglycoside required for the same level of effectiveness in the absence of salicylanilide or a derivative thereof.

13. The method of claim 1, wherein the aminoglycoside is contacted to the bacteria or is administered as a composition comprising at least 100 µM, at least 200 µM, or at least 400 µM of the aminoglycoside.

14. The method according to claim 1, wherein the tetracycline is contacted to the bacteria or is administered as a composition comprising at least 100 µM, at least 200 µM, or at least 400 µM of the tetracycline.

* * * * *